US011844895B2

(12) United States Patent
McCrea et al.

(10) Patent No.: US 11,844,895 B2
(45) Date of Patent: Dec. 19, 2023

(54) METHOD FOR REMOVING BACTERIA FROM BLOOD USING HIGH FLOW RATE

(71) Applicant: ExThera Medical Corporation, Martinez, CA (US)

(72) Inventors: Keith McCrea, Concord, CA (US); Robert Ward, Orinda, CA (US)

(73) Assignee: ExThera Medical Corporation, Martinez, CA (US)

( * ) Notice: Subject to any disclaimer, the term of this patent is extended or adjusted under 35 U.S.C. 154(b) by 788 days.

(21) Appl. No.: 16/720,720

(22) Filed: Dec. 19, 2019

(65) Prior Publication Data

US 2020/0171233 A1  Jun. 4, 2020

Related U.S. Application Data

(60) Division of application No. 15/332,801, filed on Oct. 24, 2016, now abandoned, which is a continuation of application No. PCT/US2015/026340, filed on Apr. 17, 2015.

(60) Provisional application No. 61/984,013, filed on Apr. 24, 2014.

(51) Int. Cl.
*A61M 1/36* (2006.01)
*B01J 20/32* (2006.01)
*B01J 20/28* (2006.01)
*B01J 20/26* (2006.01)

(52) U.S. Cl.
CPC ............ *A61M 1/3679* (2013.01); *B01J 20/26* (2013.01); *B01J 20/28004* (2013.01); *B01J 20/28016* (2013.01); *B01J 20/28023* (2013.01); *B01J 20/321* (2013.01); *B01J 20/3204* (2013.01); *B01J 20/3212* (2013.01); *B01J 20/3274* (2013.01); *B01J 20/3293* (2013.01); *B01J 2220/62* (2013.01)

(58) Field of Classification Search
CPC ........ A61M 1/3679; A61M 2202/0413; A61M 2202/203; A61M 1/3486; A61M 1/3692; A61M 2202/0057; B01J 20/321; B01J 20/3212; B01J 20/3293; B01J 20/28023; B01J 20/26; B01J 20/3204; B01J 20/28004; B01J 20/28016; B01J 2220/62; B01J 20/3274
See application file for complete search history.

(56) References Cited

U.S. PATENT DOCUMENTS

| | | |
|---|---|---|
| 3,782,382 A | 1/1974 | Naftulin et al. |
| 4,103,685 A | 8/1978 | Lupien et al. |
| 4,415,665 A | 11/1983 | Mosbach et al. |
| 4,430,496 A | 2/1984 | Abbott |
| 4,599,165 A | 7/1986 | Chevallet |
| 4,613,665 A | 9/1986 | Larm |
| 4,637,994 A | 1/1987 | Tani et al. |
| 4,643,896 A | 2/1987 | Asakura et al. |
| 4,820,302 A | 4/1989 | Woodroof |
| 4,955,870 A | 9/1990 | Ridderheim et al. |
| 5,116,962 A | 5/1992 | Stueber et al. |
| 5,211,850 A | 5/1993 | Shettigar et al. |
| 5,227,049 A | 7/1993 | Chevallet et al. |
| 5,318,511 A | 6/1994 | Riquier et al. |
| 5,403,917 A | 4/1995 | Boos et al. |
| 5,437,861 A | 8/1995 | Okarma et al. |
| 5,447,859 A | 9/1995 | Prussak |
| 5,476,509 A | 12/1995 | Keogh, Jr. et al. |
| 5,679,775 A | 10/1997 | Boos et al. |
| 5,753,227 A | 5/1998 | Strahilevitz |
| 6,037,458 A | 3/2000 | Hirai et al. |
| 6,159,377 A | 12/2000 | Davankov et al. |
| 6,197,568 B1 | 3/2001 | Marks et al. |
| 6,248,127 B1 | 6/2001 | Shah et al. |
| 6,312,907 B1 | 11/2001 | Guo et al. |
| 6,461,665 B1 | 10/2002 | Scholander |
| 6,544,727 B1 | 4/2003 | Hei |
| 6,559,290 B1 | 5/2003 | Nakatani et al. |
| 6,653,457 B1 | 11/2003 | Larm et al. |
| 7,179,660 B1 | 2/2007 | Kirakossian |
| 7,408,045 B2 | 8/2008 | Maruyama et al. |
| 7,695,609 B2 | 4/2010 | Soundarrajan et al. |
| 8,273,357 B2 | 9/2012 | Hacohen et al. |
| 8,663,148 B2 | 3/2014 | Larm et al. |
| 8,758,286 B2 | 6/2014 | Ward et al. |
| 9,173,989 B2 | 11/2015 | Larm et al. |

(Continued)

FOREIGN PATENT DOCUMENTS

| | | |
|---|---|---|
| CN | 1395620 A | 2/2003 |
| CN | 101370536 A | 2/2009 |

(Continued)

OTHER PUBLICATIONS

Slama T.G., Review: "Gram-negative antibiotic resistance: there is a price to pay", Critical Care 2008, 12 (Suppl 4):S4 (doi:10.1186/ccXXXX), total pp. 1-7. (Year: 2008).*
Abdul-Razzak, K. et al., "Fetal and newborn calf thymus as a source of chromatin proteins: Purification of HMG-1 and HMG-2," Preparative Biochemistry and Biotechnology, 17(1):51-61, 1987.
Alarabi, A. et al., "Treatment of pruritus in cholestatic jaundice by bilirubin- and bile acid-adsorbing resin column plasma perfusion," Scandinavian Journal of Gastroenterology, 27(3):223-6, 1992.
Alfaro et al., "Interleukin-8 in cancer pathogenesis, treatment and follow-up," Cancer Treat Rev., Nov. 2017, vol. 60:24-31 (abstract only).
Axelsson, J. et al., "Cytokines in blood from septic patients interact with surface-immobilized heparin," ASAIO Journal, 56:48-51, 2010.
Bhakdi, S. and Tranum-Jensen, J., "Alpha-toxin of *Staphylococcus aureus*," Microbiological Reviews, 55(4):733-751, 1991.

(Continued)

*Primary Examiner* — Satyendra K Singh
(74) *Attorney, Agent, or Firm* — Kilpatrick Townsend & Stockton LLP

(57) ABSTRACT

The present invention provides methods for removing a significant amount of bacteria (e.g., gram-negative bacteria and gram-positive bacteria, including bacteria with no or low affinity for heparan sulfate) from whole blood, serum or plasma using an adsorption media. The method can be used in extracorporeal treatments involving high volumetric flow rates and high linear flow rates.

14 Claims, 4 Drawing Sheets

(56) References Cited

U.S. PATENT DOCUMENTS

| | | |
|---|---|---|
| 9,408,962 B2 | 8/2016 | Ward et al. |
| 9,669,150 B2 | 6/2017 | Larm et al. |
| 9,764,077 B2 | 9/2017 | Larm et al. |
| 10,086,126 B2 | 10/2018 | Ward et al. |
| 10,188,783 B2 | 1/2019 | Larm et al. |
| 10,457,974 B2 | 10/2019 | Ward et al. |
| 10,487,350 B2 | 11/2019 | Ward et al. |
| 10,537,280 B2 | 1/2020 | McCrea et al. |
| 10,639,413 B2 | 5/2020 | McCrea et al. |
| 10,688,239 B2 | 6/2020 | Larm et al. |
| 10,786,615 B2 | 9/2020 | Ward et al. |
| 10,857,283 B2 | 12/2020 | Ward et al. |
| 11,065,378 B2 | 7/2021 | Larm et al. |
| 11,123,466 B2 | 9/2021 | Ward et al. |
| 11,266,772 B2 | 3/2022 | McCrea et al. |
| 11,306,346 B2 | 4/2022 | Ward et al. |
| 2001/0005487 A1 | 6/2001 | Kamibayashi et al. |
| 2002/0018985 A1 | 2/2002 | Eibl et al. |
| 2002/0040012 A1 | 4/2002 | Stiekema et al. |
| 2002/0058032 A1 | 5/2002 | Hirai et al. |
| 2002/0068183 A1 | 6/2002 | Huang et al. |
| 2002/0197249 A1 | 12/2002 | Brady et al. |
| 2002/0197252 A1 | 12/2002 | Brady et al. |
| 2003/0021780 A1 | 1/2003 | Smith et al. |
| 2003/0044769 A1 | 3/2003 | Ogino et al. |
| 2003/0148017 A1 | 8/2003 | Tuominen et al. |
| 2004/0054320 A1 | 3/2004 | Kissinger et al. |
| 2004/0084358 A1 | 5/2004 | O'Mahony et al. |
| 2004/0115278 A1 | 6/2004 | Putz et al. |
| 2004/0140265 A1 | 7/2004 | Lihme |
| 2004/0176672 A1 | 9/2004 | Silver et al. |
| 2004/0182783 A1 | 9/2004 | Walker et al. |
| 2004/0185553 A9 | 9/2004 | Hei |
| 2004/0202783 A1 | 10/2004 | Baumann et al. |
| 2005/0098500 A1 | 5/2005 | Collins et al. |
| 2005/0142542 A1 | 6/2005 | Hei et al. |
| 2005/0205476 A1 | 9/2005 | Chevallet et al. |
| 2005/0244371 A1 | 11/2005 | Lentz |
| 2005/0271653 A1 | 12/2005 | Strahilevitz |
| 2006/0030027 A1 | 2/2006 | Ellson et al. |
| 2006/0093999 A1 | 5/2006 | Hei |
| 2006/0252054 A1 | 11/2006 | Ping |
| 2007/0190050 A1 | 8/2007 | Davidner et al. |
| 2007/0218514 A1 | 9/2007 | Smith et al. |
| 2007/0231217 A1 | 10/2007 | Clinton et al. |
| 2008/0021365 A1 | 1/2008 | Kobayashi et al. |
| 2008/0138434 A1 | 6/2008 | Brady et al. |
| 2008/0268464 A1 | 10/2008 | Schumacher et al. |
| 2008/0314817 A1 | 12/2008 | Fujita et al. |
| 2009/0105194 A1 | 4/2009 | Flengsrud et al. |
| 2009/0136586 A1 | 5/2009 | Larm et al. |
| 2009/0173685 A1 | 7/2009 | Imai et al. |
| 2009/0186065 A1 | 7/2009 | Tillman et al. |
| 2009/0206038 A1 | 8/2009 | Thomas |
| 2009/0246800 A1 | 10/2009 | Mattingly et al. |
| 2009/0325276 A1 | 12/2009 | Battrell et al. |
| 2010/0021622 A1 | 1/2010 | Meng et al. |
| 2010/0040546 A1 | 2/2010 | Hyde et al. |
| 2010/0069816 A1 | 3/2010 | Brady et al. |
| 2010/0079360 A1 | 4/2010 | McLaughlin et al. |
| 2010/0098666 A1 | 4/2010 | Wright |
| 2010/0112725 A1 | 5/2010 | Babu et al. |
| 2010/0145317 A1 | 6/2010 | Laster et al. |
| 2010/0216226 A1 | 8/2010 | Hyde et al. |
| 2010/0217173 A1 | 8/2010 | Hyde et al. |
| 2010/0239673 A1 | 9/2010 | Linhardt et al. |
| 2010/0249689 A1 | 9/2010 | Larm et al. |
| 2010/0276359 A1 | 11/2010 | Ippommatsu et al. |
| 2010/0291588 A1 | 11/2010 | McDevitt et al. |
| 2010/0326916 A1 | 12/2010 | Wrazel et al. |
| 2011/0137224 A1 | 6/2011 | Ibragimov |
| 2011/0150911 A1 | 6/2011 | Choo et al. |
| 2011/0171713 A1 | 7/2011 | Bluchel et al. |
| 2011/0184377 A1 | 7/2011 | Ward et al. |
| 2011/0224645 A1 | 9/2011 | Winqvist et al. |
| 2012/0040429 A1 | 2/2012 | Federspiel et al. |
| 2012/0219561 A1 | 8/2012 | Alt et al. |
| 2012/0305482 A1 | 12/2012 | McCrea et al. |
| 2013/0102948 A1 | 4/2013 | Reich et al. |
| 2013/0131423 A1 | 5/2013 | Wang et al. |
| 2014/0012097 A1 | 1/2014 | McCrea et al. |
| 2014/0074007 A1 | 3/2014 | McNeil |
| 2014/0131276 A1 | 5/2014 | Larm et al. |
| 2014/0231357 A1 | 8/2014 | Ward et al. |
| 2015/0111849 A1 | 4/2015 | McCrea et al. |
| 2015/0260715 A1 | 9/2015 | Hu et al. |
| 2016/0022898 A1 | 1/2016 | Larm et al. |
| 2016/0082177 A1 | 3/2016 | Ward et al. |
| 2016/0084835 A1 | 3/2016 | Ward et al. |
| 2016/0101229 A1 | 4/2016 | McCrea et al. |
| 2016/0214935 A1 | 7/2016 | Hutchinson et al. |
| 2016/0243525 A1 | 8/2016 | Song et al. |
| 2016/0331886 A1 | 11/2016 | Ward et al. |
| 2017/0035956 A1 | 2/2017 | McCrea et al. |
| 2017/0073727 A1 | 3/2017 | Ward et al. |
| 2017/0340803 A1 | 11/2017 | Larm et al. |
| 2018/0117237 A1 | 5/2018 | Brugger et al. |
| 2018/0361050 A1 | 12/2018 | Ward et al. |
| 2019/0038826 A1 | 2/2019 | McCrea et al. |
| 2019/0143027 A1 | 5/2019 | Larm et al. |
| 2020/0023001 A1 | 1/2020 | Ebong et al. |
| 2020/0056221 A1 | 2/2020 | Ward et al. |
| 2020/0297913 A1 | 9/2020 | Larm et al. |
| 2020/0338256 A1 | 10/2020 | Ward et al. |
| 2022/0072038 A1 | 3/2022 | Ward et al. |

FOREIGN PATENT DOCUMENTS

| | | |
|---|---|---|
| CN | 101784294 A | 7/2010 |
| CN | 102740859 A | 10/2012 |
| CN | 102791307 | 11/2012 |
| CN | 106255520 A | 12/2016 |
| CN | 206345699 U | 7/2017 |
| DE | 4217917 A1 | 12/1993 |
| EP | 0 306 617 A | 3/1989 |
| EP | 0 321 703 A | 6/1989 |
| EP | 0533946 A1 | 3/1993 |
| EP | 0 616 845 A | 9/1994 |
| EP | 0 810 027 A | 12/1997 |
| EP | 1044696 A2 | 10/2000 |
| EP | 1 057 529 A | 12/2000 |
| EP | 1 110 602 A | 6/2001 |
| EP | 1 219 639 A | 7/2002 |
| EP | 2087916 A1 | 8/2009 |
| EP | 2556849 A1 | 2/2013 |
| GB | 2 172 812 A | 10/1986 |
| JP | 54-127493 U | 9/1979 |
| JP | 58-053757 A | 3/1983 |
| JP | 58-146354 A | 8/1983 |
| JP | 4-89500 A | 3/1992 |
| JP | 6040926 A | 2/1994 |
| JP | 6-505248 A | 6/1994 |
| JP | 7-178161 A | 7/1995 |
| JP | 96-510166 A | 10/1996 |
| JP | 11-502703 A | 3/1999 |
| JP | 2000-086688 A | 3/2000 |
| JP | 2000-217575 A | 8/2000 |
| JP | 2000-515543 A | 11/2000 |
| JP | 2001-190273 A | 7/2001 |
| JP | 2002-505101 A | 2/2002 |
| JP | 2002-509518 A | 3/2002 |
| JP | 2003-128502 A | 5/2003 |
| JP | 2003-520048 A | 7/2003 |
| JP | 2005-514127 A | 5/2005 |
| JP | 2005-519744 A | 7/2005 |
| JP | 2005-532130 A | 10/2005 |
| JP | 2009-521413 A | 6/2009 |
| JP | 2010-518046 A | 5/2010 |
| JP | 2010-530288 A | 9/2010 |
| JP | 2011-509083 A | 3/2011 |
| JP | 2012-501708 A | 1/2012 |
| JP | 2013-512078 A | 4/2013 |
| JP | 2014-500735 A | 1/2014 |
| JP | 2014-523914 A | 9/2014 |

(56) References Cited

FOREIGN PATENT DOCUMENTS

| KR | 10-2008-0077405 A | 8/2008 |
|---|---|---|
| WO | 91/04086 A | 4/1991 |
| WO | 92/14361 A1 | 9/1992 |
| WO | 94/26399 A1 | 11/1994 |
| WO | 95/05400 | 2/1995 |
| WO | 96/29083 A1 | 9/1996 |
| WO | 96/40857 A1 | 12/1996 |
| WO | 97/35660 A1 | 10/1997 |
| WO | 98/05341 A1 | 2/1998 |
| WO | 98/29727 A2 | 7/1998 |
| WO | 99/06086 A1 | 2/1999 |
| WO | 99/45104 A3 | 11/1999 |
| WO | 00/23792 | 4/2000 |
| WO | 00/038763 | 7/2000 |
| WO | 00/66260 A | 11/2000 |
| WO | 01/18060 A | 3/2001 |
| WO | 01/53525 A2 | 7/2001 |
| WO | 02/060512 | 8/2002 |
| WO | 03/033143 A1 | 4/2003 |
| WO | 2003/057356 A2 | 7/2003 |
| WO | 2003/078023 A1 | 9/2003 |
| WO | 2004/008138 A2 | 1/2004 |
| WO | 2004/009798 A2 | 1/2004 |
| WO | 2005/021799 A2 | 3/2005 |
| WO | 2006/012885 A1 | 2/2006 |
| WO | 2007/058592 A1 | 5/2007 |
| WO | 2007/069983 A1 | 6/2007 |
| WO | 2007/101064 A2 | 9/2007 |
| WO | 2007/146162 A2 | 12/2007 |
| WO | 2008/095905 A2 | 8/2008 |
| WO | 2008/157570 A2 | 12/2008 |
| WO | 2009/086343 A2 | 7/2009 |
| WO | 2009/121959 A1 | 10/2009 |
| WO | 2010/029317 A2 | 3/2010 |
| WO | 2011/068897 A1 | 6/2011 |
| WO | 2011/100354 A1 | 8/2011 |
| WO | 2012/051595 A1 | 4/2012 |
| WO | 2012/112724 A1 | 8/2012 |
| WO | 2012/172341 A2 | 12/2012 |
| WO | 2013/012924 A2 | 1/2013 |
| WO | 2013/188073 A1 | 12/2013 |
| WO | 2014/209782 A1 | 12/2014 |
| WO | 2015/069942 A1 | 5/2015 |
| WO | 2015/164198 A1 | 10/2015 |
| WO | 2017/001357 A1 | 1/2017 |
| WO | 2020/231830 A1 | 11/2020 |
| WO | 2021/119195 A1 | 6/2021 |
| WO | 2021/119197 A1 | 6/2021 |
| WO | 2022/216510 A1 | 10/2022 |

OTHER PUBLICATIONS

Bindslev. L. et al., "Treatment of acute respiratory failure by extracorporeal carbon dioxide elimination performed with a surface heparinized artificial lung," Anesthesiology, 67(1):117-120, 1987.
Bjorklund, M. et al., Abstract of "Synthesis of silica-based heparin-affinity adsorbents," J. Chrom. A., 728(1-2):149-169, 1996.
Brat, D. et al., "The role of interleukin-8 and its receptors in gliomagenesis and tumoral angiogenesis," Neuro-oncology, 7(2):122-133, 2005.
Celik, T. et al., "Treatment of lyme neuroborreliosis with plasmapheresis," J. Clinical Apheresis, 31:476-478, 2016.
Chase, H., "Affinity separations utilising immobilised monoclonal antibodies—a new tool for the biochemical engineer," Chemical Engineering Science, 39(7-8):1099-1125, 1984.
Chen, Y. et al., "Microbial subversion of heparin sulfate proteoglycans," Mol. Cells, 26:415-426, 2008.
Dixon, T. et al., "Anthrax," New England Journal of Medicine, 341(11):815-826, 1999.
Dubreuil, J. et al., "Effect of heparin binding on Helicobacter pylori resistance to serum," J. Med. Micro., 53:9-12, 2004.
Francy, D. et al., "Comparison of filters for concentrating microbial indicators and pathogens in lake water samples," Applied and Environmental Microbiology, 79(4):1342-52, 2012.
Fujita, M. et al., "Adsorption of inflammatory cytokines using a heparin-coated extracorporeal circuit," Artificial Organs, 26(12):1020-1025, 2002.
Garg, L. et al., "Isolation and separation of HMG proteins and histones H1 and H5 and core histones by col. chromatography on phosphocellulose," Protein Expression and Purification, 14(2):155-159, 1998.
GE Healthcare, "Size exclusion chromatography columns and resins, Selection guide," 2010, retrieved online at <<https://cdn.gelifesciences.com/dmm3bwsv3/AssetStream.aspx?mediaformatid=10061&destinationid=10016&assetid=13947>> on Jun. 27, 2019, 10 pages.
Ghannoum, M. et al., "Extracorporeal treatment for carbamazepine poisoning: Systematic review and recommendations from the EXTRIP workgroup," Clinical Toxicology, 52:993-1004, 2014.
Haase, M. et al., "The effect of three different miniaturized blood purification devices on plasma cytokine concentration in an ex vivo model of endotoxinemia," Int. J. Artif. Organs, 31(8):722-729, 2008.
Hirmo, S. et al., "Sialyglycoconjugate- and proteoglycan-binding microbial lectins," Institute of Medical Microbiology, University of Lund, (Online). Retrieved Oct. 19, 1997 (Retrieved on Mar. 16, 2004). Retrieved from the Internet: <URL: http//www.plab.ku.dk/tcbh/Lectins12/Hirmo/paper.htm>.
International Preliminary Report on Patentability, dated Aug. 21, 2013, PCT Application No. PCT/US2012/025316; 8 pages.
International Search Report; PCT/SE2006/001421 dated Mar. 30, 2007.
International Search Report; PCT/US2010/058596 dated Mar. 29, 2011.
International Search Report; PCT/US2011/024229 dated May 30, 2011.
International Search Report; PCT/US2012/025316 dated May 23, 2012.
International Search Report; PCT/US2013/042377 dated Sep. 9, 2013.
International Search Report; PCT/US2014/043358 dated Dec. 1, 2014.
International Search Report; PCT/US2014/064419 dated Feb. 12, 2015.
International Search Report; PCT/US2015/026340 dated Jul. 28, 2015.
International Search Report; PCT/US2015/051239 dated Dec. 17, 2015.
International Search Report; PCT/US2016/057121 dated Dec. 30, 2016.
International Search Report; PCT/US2017/058536; dated Jan. 17, 2018.
Kadam, P. et al., "Jarisch-Herxheimer Reaction in a Patient with Disseminated Lyme Disease," Journal of Case Reports, 3(2):362-365, 2013.
Kenig, M. et al., "Identification of the heparin-binding domain of TNF-alpha and its use for efficient TNF-alpha purification by heparin-Sepharose affinity chromatography," J. Chromatography B, 867:119-125, 2008.
Keuren, J. et al., "Thrombogenecity of polysaccharide-coated surfaces," Biomaterials, 24:1917-24, 2003.
Kim et al., "Role of the heparin in regulating a transcapillary exchange in far north conditions," Bulletin of the Siberian Branch of the Russian Academy of Medical Sciences, 2(108), 2003.
Kishimoto, S. et al., "Human stem cell factor (SCF) is a heparin-binding cytokine," J. Biochem., 145(3):275-278, 2009.
Kumari, N. et al., "Role of interleukin-6 in cancer progression and therapeutic resistance," Tumour Biol., Sep. 2016, vol. 37(9), pp. 11553-11572 (abstract only).
Larm, O. et al., "A new non-thrombogenic surface prepared by selective covalent binding of heparin via a modified reducing terminal residue," Biomater Med Devices Artif Organs, 11(2&3):161-173, 1983.

(56) References Cited

OTHER PUBLICATIONS

Lemaire, M. et al., "Treatment of paediatric vancomycin intoxication: a case report and review of the literature," NDT Plus, 3:260-264, 2010.
Lian, S. et al., "Elevated expression of growth-regulated oncogene-alpha in tumor and stromal cells predicts unfavorable prognosis in pancreatic cancer," Medicine, Jul. 2016, 95(30), pp. 1-8.
Lopatkin et al., "Efferent methods in medicine, M.," Medicine, pp. 266, 272-273, 276-279, 1989.
Low, R. et al., "Protein n, a primosomal DNA replication protein of *Escherichia coli*," Journal of Biological Chemistry, 257(11):6242-6250, 1982.
Mandal, C. and Mandal, C. "Sialic acid binding lectins," Experientia, 46:433-439, 1990.
Mariano, F. et al, "Tailoring high-cut-off membranes and feasible application in sepsis-associated acute renal failure: in vitro studies," Nephrol Dial Transplant, 20:1116-1126, 2005.
Mattsby-Baltzer, I. et al., "Affinity apheresis for treatment of bacteremia caused by *Staphylococcus aureus* and/or methicillin-resistant *S. aureus* (MRSA)," J. Microbiol. Biotechnol., 21(6):659-664, 2011.
Millen, H. et al., "Glass wool filters for concentrating waterborne viruses and agricultural zoonotic pathogens," J. Vis. Exp., 61:e3930, 2012.
Nadkarni, V. et al., Abstract of "Directional immobilization of heparin onto beaded supports," Anal. Biochem., 222(1):59-67, 1994.
Ofek, I. and Beachey, E., "Mannose binding and epithelial cell adherence of *Escherichia coli*," Infection and Immunity, 22(1):247-254, 1978.
Park, P. et al., "Activation of Syndecan-1 ectodomain shedding by *Staphylococcus aureus* α-toxin and β-toxin," J. Biol. Chem., 279(1):251-258, 2004.
Popova, T. et al., "Acceleration of epithelial cell syndecan-1 shedding by anthrax hemolytic virulence factors," BMC Microbiolgy, 6:8, pp. 1-16, 2006.
Rauvala, H. et al., "Isolation and some characteristics of an adhesive factor of brain that enhances neurite outgrowth in central neurons," Journal of Biological Chemistry, 262(34):16625-16635, 1987.
Rauvala, H. et al., "The adhesive and neurite-promoting molecule p30: Analysis of the amino-terminal sequence and production of antipeptide antibodies that detect p30 at the surface of neuroblastoma cells and of brain neurons," Journal of Cell Biology, 107(6,1):2293-2305, 1988.
Riesenfeld, J. and Roden, L., "Quantitative analysis of N-sulfated, N-acetylated, and unsubstituted glucosamine amino groups in heparin and related polysaccharides," Anal Biochem, 188:383-389, 1990.
Sagnella, S. et al., "Chitosan based surfactant polymers designed to improve blood compatibility on biomaterials," Colloids and Surfaces B: Biointerfaces, 42:147-155, 2005.
Salek-Ardakani, S. et al., "Heparin and heparan sulfate bind interleukin-10 and modulate its activity," Blood, 96:1879-1888, 2000.
Salmivirta, M. et al., "Neurite growth-promoting protein (Amphoterin, p30) binds syndecan," Experimental Cell Research, 200:444-451, 1992.
Sanchez, J. et al., "Control of contact activation on end-point immobilized heparin: The role of antithrombin and the specific antithrombin-binding sequence," J. Bio. Mat. Res., 29:665-661, 1995.
Sasaki, H. et al., Abstract: "Improved method for the immobilization of heparin," J. Chrom., 400:123-32, 1987.
Sato, T. et al., "Experimental study of extracorporeal perfusion for septic shock," Asaio Journal, 39(3):M790-M793, 1993.
Schefold, J. et al., "A novel selective extracorporeal intervention in sepsis: immunoadsorption of endotoxin, interleukin 6, and complement-activating product 5A," Shock, 28(4):418-425, 2007.
Sharon, N., "Bacterial lectins, cell-cell recognition and infectious disease," FEBS letters, 217(2):145-157, 1987.
Swartz, M., "Recognition and management of anthrax—an update," New Engl. J. Med., 345(22):1621-1626, 2001.
Thomas, R. and Brooks, T., "Common oligosaccharide moieties inhibit the adherence of typical and atypical respiratory pathogens," Journal of Microbiology, 53:833-840, 2004.
Utt, M. et al., "Identification of heparan sulphate binding surface proteins of Helicobacter pylori: inhibition of heparan sulphate binding with sulphated carbohydrate polymers," J. Med. Microbiol., 46:541-546, 1997.
Wang, H. et al., "HMG-1 as a late mediator of endotoxin lethality in mice," Science, 285:248-251, 1999.
Ward, R. et al., "Specificity of adsorption in a prototype whole blood affinity therapy device for removal of *Staphylococcus aureus*," Society for Biomaterials 2013 Annual Meeting and Exposition, Apr. 10, 2013, p. 1.
Waugh D. and Wilson, C., "The interleukin-8 pathway in cancer," Clin. Cancer Res., 14(21):6735-41, 2008.
Webb, L. et al., "Binding to heparan sulfate or heparin enhances neutrophil responses to interleukin 8," PNAS USA, 90:7158-62, 1993.
Weber, V. et al., "Development of specific adsorbents for human tumor necrosis factor-α: influence of antibody immobilization on performance and biocompatibility," Biomacromolecules, 6:1864.1870, 2005.
Weir, D., "Carbohydrates as recognition molecules in infection and immunity," FEMS Microbiology Immunology, 47:331-340, 1989.
Wendel, H. and Ziemer, G., "Coating-techniques to improve the hemocompatibility of artificial devices used for extracorporeal circulation," European Journal of Cardio-thoracic Surgery, 16:342-350, 1999.
Yu, J. et al., "Adhesion of coagulase-negative staphylococci and adsorption of plasma proteins to heparinized polymer surfaces," Biomaterials, 15(10):805-814, 1994.
Zhou, M. and Reznikoff, W., Abstract: "Heparin-agarose aqueous ethanol suspension," J. Mol. Bio., 271(3):12, 1997.
Andrade-Gordon, P. et al., "Interaction of heparin with plasminogen activators and plasminogen: effects on the activation of plasminogen," Biochemistry, 25(14):4033-4040, 1986.
Andreasen, P.A. et al., "The plasminogen activation system in tumor growth, invasion, and metastasis," Cellular and Molecular Life Sciences, 57(1):25-40, 2000.
Ascencio, F. et al., "Affinity of the gastric pathogen Helicobacter pylori for the N-sulphated glycosaminoglycan heparan sulphate," J. Med. Microbiol., 38:240-244, 1993.
Bartlett, A. and P. Park, "Proteoglycans in host-pathogen interactions: molecular mechanisms and therapeutic implications," Expert Rev. Mol. Med., 12(e5):1-33, 2015.
Choong, P.F. et al., "Urokinase plasminogen activator system: a multifunctional role in tumor progression and metastasis," Clinical Orthopaedics and Related Research, 415(Suppl):S46-58, 2003.
Era, K. et al., "Development of Systems for Passive and Active CAVH," J. Japanese Society for Dialysis Therapy, 19(2):175-181, 1986.
Frick, I. et al., "Interactions between M proteins of *Streptococcus pyogenes* and glycosaminoglycans promote bacterial adhesion to host cells," Eur. J. Biochem, 270(10):2303-11, 2003.
International Search Report; PCT/US2020/032150; dated Jul. 24, 2020.
International Search Report; PCT/US2020/064110; dated Apr. 13, 2021.
International Search Report; PCT/US2020/064112; dated Mar. 10, 2021.
International Search Report; PCT/US2022/022748; dated Aug. 17, 2022.
Murphy, J.W. et al., "Structural and functional basis of CXCL 12 (stromal cell-derived factor-1 a) binding to heparin," Journal of Biological Chemistry, 282(13):10018-10027, 2007.
Office Action dated Jun. 23, 2020 in Japanese Patent Application No. 2017-515161, with English translation, retrieved from <https://globaldossier.uspto.gov/#/details/JP/2017515161/A/129021> on Aug. 13, 2020.

(56) References Cited

OTHER PUBLICATIONS

Ok, S. et al., "Emodin inhibits invasion and migration of prostate and lung cancer cells by downregulating the expression of chemokine receptor CXCR4," Immunopharmacology and Immunotoxicology, 34(5):768-778, 2012.

Sanaka, T. et al., "Continuous Arteriovenous Hemofiltration," Artificial Organs, 14(5):1822-1830, 1985.

Smorenburg, S.M. et al., "The complex effects of heparins on cancer progression and metastasis in experimental studies," Pharmacological Reviews, 53(1):93-106, 2001.

Stevens, K. et al., "Hydrophilic surface coatings with embedded biocidal silver nanoparticles and sodium heparin for central venous catheters," Biomaterials, 32(5):1264-1269, 2011.

Tonnaer, E. et al., "Involvement of glycosaminoglycans in the attachment of pneumococci to nasopharyngeal epithelial cells," Microbes and Infection, 8:316-322, 2006, available online Sep. 16, 2005.

Wadstrom, T. and A. Ljungh, "Glycosaminoglycan-binding microbial proteins in tissue adhesion and invasion: key events in microbial pathogenicity," J. Med. Microbiol., 48(3):223-233, 1999.

* cited by examiner

*100x magnification*

*100x magnification*

METHOD FOR REMOVING BACTERIA FROM BLOOD USING HIGH FLOW RATE

CROSS-REFERENCE TO RELATED APPLICATIONS

The present application is a division of U.S. application Ser. No. 15/332,801, pending, filed Oct. 24, 2016 which is a continuation of PCT/US2015/026340, filed Apr. 17, 2015, which application claims priority to U.S. Provisional Patent Application No. 61/984,013, filed Apr. 24, 2014, the teachings of which are hereby incorporated by reference in their entirety for all purposes.

BACKGROUND OF THE INVENTION

Bloodstream infection, or bacteremia, is a major challenge in the Intensive Care Unit (ICU). Bacteremia can quickly lead to septic shock, meningitis, endocarditis, osteomyelitis and other metastatic complications. *Staphylococcus aureus, P. aeruginosa* and Enterobacteriacea are the most common bacteria responsible for bacteremia and nosocomial infections. Severity of outcome for bacteremic patients is correlated to both the bacterial load and duration of bacteremia. For example, a quantitative RT-PCR study of *E. coli* and *S. aureus* bacteremia patients showed that when the number of rDNA increased to over 1,238 copies/ml, mortality increased from 14.3% to 42.9% and septic shock increased from 31.4% to 85.7%. It was also found that a high blood concentration of *N. meningitides* is correlated with prolonged hospitalization, limb or tissue loss, the need for dialysis, and patient mortality. Another study showed that the severity of Pneumococcal pneumonia correlated with bacterial load in the blood: the mortality for patients with over 1000 *S. pneumoniae* DNA copies/ml of blood was 25.9% vs. 6.1% for patients exhibiting less than 1000 copies/ml. In yet another study, a follow-up positive blood culture between 48 and 96 hours after initial diagnosis was shown to be the strongest predictor of complicated *S. aureus* bacteremia. Compounding the difficulty of effective bacteremia treatment is the often delayed administration of appropriate antibiotic therapy. For each hour of delay in treatment the mortality risk increases over 7%.

The conventional strategy for combating bacterial infections is to administer active drugs that specifically kill bacteria while minimizing damage to host tissue. This is a major challenge as some of the more effective antibiotics available today are quite toxic. For example, vancomycin is nephrotoxic, and may soon be contraindicated for patients undergoing extracorporeal oxygenation. Even if new antibiotics are successfully developed to address current drug resistance, new superbugs will continue to emerge. Clearly, new strategies for combating infection are needed, in addition to drug discovery.

Drug-resistant pathogens are a growing threat to the healthcare system. The CDC has recently warned of the emergence of carbapenem-resistant Enterobacteriacea (CRE; "super bugs"). The mortality rate for CRE bacteremia can be as high as 50%. Resistance of CREs to even the strongest available antibiotics leaves clinicians with few treatment options. The incidence of hospital-acquired CRE infections has increased 400% over the last 10 years. Currently, CRE bacteremias are mostly nosocomial infections, but there is concern that the incidence of community acquired CRE could increase. Today, the only strategy is to reduce CRE infections is through education and prevention.

There is a need for a safe, broad-spectrum technology that can quickly reduce bacterial load, and shorten the duration of bacteremia. The present invention satisfies this and other needs by providing a high-surface-area extracorporeal affinity adsorption media that can quickly and safely remove pathogens from whole blood or whole serum.

BRIEF SUMMARY OF THE INVENTION

The present invention provides methods that can quickly reduce bacterial load, and shorten the duration of bacteremia even without first identifying the type of bacteria present in the blood.

In some aspects, provided herein is an ex vivo method for removing bacteria from a sample taken from a subject who is suspected of being infected with bacteria. The method comprising, consisting essentially of or consisting of: contacting a sample taken from the subject with an adsorption media to allow the formation of an adhering complex, wherein the adhering complex comprises bacteria and the adsorption media; and separating the sample from the adhering complex to produce the sample with a reduced amount of bacteria. Typically, the adsorption media is contained within a column, a container or cartridge.

In some embodiments, the sample is selected from the group consisting of whole blood, serum and plasma. In other embodiments, the sample is whole blood.

In some embodiments, the adsorption media is a solid substrate of high surface area having a hydrophilic surface that is free of a polysaccharide adsorbent. In some instances, the solid substrate comprises a plurality of rigid polymer bead. In some embodiments, the rigid polymer bead is a member selected from the group consisting of polyurethane, polymethylmethacrylate, polyethylene or co-polymers of ethylene and other monomers, polyethylene imine, polypropylene, and polyisobutylene. In other embodiments, the solid substrate comprises one or a plurality of hollow fibers or yarn.

In some embodiments, the hydrophilic surface is a cationic surface. In other embodiments, the hydrophilic surface is a neutrally charged surface.

In some embodiments, the bacteria in the sample are reduced by about 20% to about 99.9%. In other embodiments, the bacteria in the sample are reduced by about 20% to about 40%.

In some embodiments, the bacterium is a gram-negative bacterium. In other embodiments, the bacterium is a gram-positive bacterium. In other embodiments, the bacteria is selected from the group consisting of *Escherichia coli, Klebsiella pneumoniae*, carbapenem-resistant *Escherichia coli*, carbapenem-resistant *Klebsiella pneumoniae*, and extended spectrum beta-lactamase *Klebsiella pneumoniae, Enterococcus faecium, Acinetobacter baumannii*, and methicillin-resistant *Staphylococcus aureus* (MRSA). In yet other embodiments, the bacterium is selected from the group consisting of *Staphylococcus aureus*, methicillin-resistant *Staphylococcus aureus* (MRSA), and *Escherichia coli*.

In some embodiments, the cationic surface of the adsorption media forms an adhering complex with bacteria selected from the group consisting of *Escherichia coli, Klebsiella pneumoniae*, carbapenem-resistant *Escherichia coli*, carbapenem-resistant *Klebsiella pneumoniae*, and extended spectrum beta-lactamase *Klebsiella pneumoniae, Enterococcus faecium, Acinetobacter baumannii*, and methicillin-resistant *Staphylococcus aureus* (MRSA). In other embodiments, the neutrally charged surface forms an adhering complex with bacteria selected from the group consisting of

*Staphylococcus aureus*, methicillin-resistant *Staphylococcus aureus* (MRSA), and *Escherichia coli*.

In some aspects, provided herein is an ex vivo method for removing bacteria from a sample taken from a subject who is suspected of being infected with bacteria, wherein the bacteria are known to have a low affinity or no affinity for heparan sulfate. The method comprising, consisting essentially of or consisting of: contacting a sample taken from a subject with an adsorption media to allow the formation of an adhering complex, wherein the adsorption media is a solid substrate of high surface area having at least one polysaccharide adsorbent on the surface thereof and separating the sample from the adhering complex to produce the sample with a reduced amount of bacteria. The adhering complex comprises bacteria and the adsorption media. Typically, the adsorption media is contained within a column, a container or cartridge. In certain aspects, the sample exits the column, the container or the cartridge, and the adhering complex remains behind.

In some embodiments, the sample is selected from the group consisting of whole blood, serum and plasma. In other embodiments, the sample is whole blood.

In some embodiments, the solid substrate comprises a plurality of rigid polymer bead. In some instances, the rigid polymer bead is a member selected from the group consisting of polyurethane, polymethylmethacrylate, polyethylene or co-polymers of ethylene and other monomers, polyethylene imine, polypropylene, and polyisobutylene. In other embodiments, the solid substrate comprises one or a plurality of hollow fibers.

In some embodiments, the at least polysaccharide absorbent is a member selected from the group consisting of heparin, heparan sulfate, hyaluronic acid, sialic acid, carbohydrates with mannose sequences, and chitosan. In other embodiments, the at least polysaccharide absorbent is heparin or heparan sulfate. In some instances, the at least polysaccharide absorbent is heparin.

In some embodiments, the beads are coated with about 0.27 mg to about 10 mg heparin per gram of bead. In other embodiments, the bead is coated with 2±0.5 mg heparin per gram of bead.

In some embodiments, the bacteria in the sample are reduced by about 20% to about 99.9%. In other embodiments, the bacteria in the sample are reduced by about 20% to about 40%.

In some embodiments, the bacteria are gram-negative bacteria. In other embodiments, the bacteria are gram-positive bacteria. In yet other embodiments, the bacteria is selected from the group consisting of *Escherichia coli*, *Klebsiella pneumoniae*, *Acinetobacter baumannii*, *Enterococcus faecium*, carbapenem-resistant *Escherichia coli*, carbapenem-resistant *Klebsiella pneumoniae*, and extended spectrum beta-lactamase *Klebsiella pneumoniae*.

In some aspects, provided herein is an ex vivo method for removing bacteria from a sample taken from a subject undergoing dialysis or extracorporeal oxygenation. The method comprising, consisting essentially of, or consisting of: contacting a sample taken from a subject with an adsorption cartridge comprising adsorption media, wherein the adsorption cartridge is in series with a dialysis cartridge or oxygenator to allow the formation of an adhering complex and separating the sample from the adhering complex to produce the sample with a reduced amount of bacteria. The adhering complex comprises bacteria and adsorption media. Typically, the adsorption media is contained within a column, a container or cartridge. In certain aspects, the sample exits the column, the container or the cartridge, and the adhering complex remains behind.

In some embodiments, the sample has a total blood volume of less than 200 ml.

In some embodiments, the adsorption cartridge has a column height between 1 cm-50 cm. In some embodiments, the adsorption cartridge has a column diameter between 1 cm-50 cm.

In some embodiments, the adsorption cartridge is proximal to the subject compared to the dialysis cartridge. In other embodiments, the adsorption cartridge is distal to the subject compared to the dialysis cartridge.

These and other aspects, objects and advantages will become more apparent when read with the figures and the detailed description which follow.

BRIEF DESCRIPTION OF THE DRAWINGS

FIG. 1A shows the adsorption media and FIG. 1B shows an image of a human blood smear.

DETAILED DESCRIPTION OF THE INVENTION

Figure 1A:
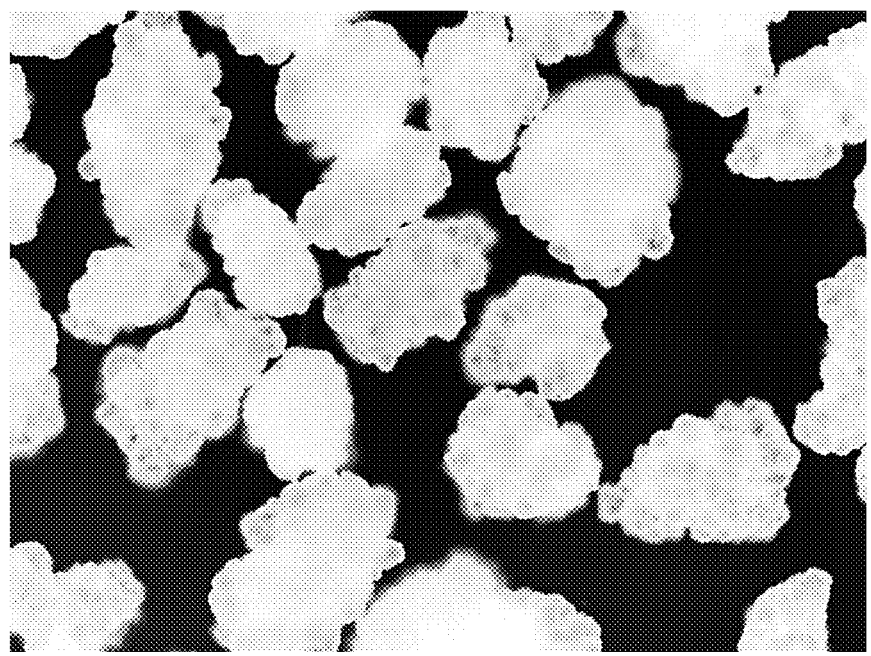
FIGS. 1A-B show a comparison of the adsorption media and human blood.

The present invention is based, in part, on the discovery of an adsorption media that is effective for removing a significant amount of bacteria (e.g., gram-negative bacteria and gram-positive bacteria, including bacteria with no known affinity or low affinity for heparan sulfate) from blood (e.g., whole blood and blood serum). In addition, the adsorption media can be used in extracorporeal treatments involving high volumetric flow rates and high linear flow rates. Typically, the adsorption media is contained within a column, a container or cartridge. In certain aspects, the sample exits the column, the container or the cartridge, and an adhering complex remains behind.

A first aspect of the present invention provides a method for the removal of bacteria from blood, such as mammalian blood, by contacting the blood with a solid substrate. The inventors have found that the surface architecture of the solid substrate is effective for removing pathogens such as bacterial pathogens or viruses.

The substrate of the present invention possesses sufficiently large interstitial dimensions to permit a high flow rate of blood over the substrate without a large pressure drop. For instance, as blood is taken from a mammalian patient, it is passed over the substrate at a flow rate whereby the delivery of adsorbates to the surface of the adsorbent bed is characterized primarily by forced convection. Substrates suited for convection transport, generally rely on macroscopic "channels" or visible interstices between solid, essential nonporous material, such as particles, beads, fibers, yarn, reticulated foams, or optionally spiral-wound dense membranes.

This is in contrast to highly porous adsorbent media (e.g., porous silica, Sephadex®, crosslinked polystyrene and other size exclusion media), and many other microporous media that use the much slower process of molecular diffusion.

Adsorption substrates that depend on diffusion transport are generally composed of porous materials with microscopic pores and an extremely high internal surface area.

I. Definitions

The term "extracorporeal therapy" includes a medical procedure that is conducted outside the body i.e., ex vivo. In some instances, extracorporeal therapies include methods in which a bodily fluid such as blood is taken from the individual and desired products such as, but not limited to, oxygen, blood-anticoagulants, anesthetics, and the like are added to the body fluid before it is returned to the individual. In other instances, an extracorporeal therapy includes removing undesired products like naturally occurring toxins, poisons or viruses from the body or the body fluids. Non-limiting examples of extracorporeal therapies include apheresis, autotransfusion, hemodialysis, hemofiltration, plasmapheresis, extracorporeal circulation (ECC), extracorporeal life support (ECLS) extracorporeal membrane oxygenation (ECMO), and cardiopulmonary bypass.

The term "high flow rate" or "high flow condition" includes a flow rate or velocity of blood that is above the diffusion limit.

The term "adsorption media" includes a material to which a cell, organism, virus, pathogen, polypeptide, polynucleotide, chemical molecule, biological molecule can adhere to the surface thereof and be removed from a sample such as blood.

The term "adhering complex" includes a complex of at least two molecules wherein the first molecule is attached (e.g., linked, coupled or bound) to a surface such as a substrate and the second molecule is attached to the first molecule. For example, a pathogen or virus can adhere to heparin to form an adhering complex. Typically, in the methods of the present invention, the adhering complex remains behind and the sample is cleansed of the patthogen or virus.

The term "high surface area" includes the property of having a large specific surface area to volume ratio.

The term "adsorbent" includes a solid substrate with a chemical compound, a biological molecule, or a material that is attached (e.g., linked, coupled or bound) thereto. In certain instances, the adsorbent is the solid substrate itself. In one embodiment, an adsorbent is a polymer resin with a polysaccharide such as heparin bound thereto. The substrate can be a polymer bead, fiber or yarn.

The term "rigid polymer bead" refers to a bead, granule, pellet, sphere, particle, microcapsule, sphere, microsphere, nanosphere, microbead, nanobead, microparticle, nanoparticle, and the like that is made from a polymer resin. A polymer bead is useful as a substrate.

The term "fiber" or "yarn" is useful as a soild substrate. The fiber or yarn can be made of a synthetic polymer or a natural polymer or a mixture thereof. In certain instances, an originally porous hollow fiber or yarn is rendered dense or non-porous before, during or after binding heparin or other adsorbents to the outer and/or inner surfaces thereof.

The term "carbohydrate" refers to a molecule containing carbon, hydrogen and oxygen atoms, and usually with the empirical formula $C_x(H_2O)_y$, where x and y are different numbers. Examples of carbohydrates includes monosaccharides, disaccharides, oligosaccharides, and polysaccharides.

The term "polysaccharide" refers to a molecule of monosaccharide units joined together by glycosidic bonds, and having an empirical formula of $C_x(H_2O)_y$, where x is between 200 to about 3000.

The term "hydrophilic surface" includes a surface with a water contact angle less than 90° when the surface is flat.

The term "low affinity to heparan sulfate" in the context of a bacteria, refers to the low binding affinity of the bacteria for heparan sulfate. In some embodiments, the binding affinity is determined using standard assays, such as an enzyme-linked immunosorbent assay (ELISA) for heparan sulfate. In other embodiments, the binding affinity is determined based on a predictive analysis, such as an analysis of putative heparan sulfate binding proteins expressed by the pathogen, e.g., bacteria. The term "no affinity for heparan sulfate" refers to a bacteria having no binding affinity for or a lower than detectable affinity for heparan sulfate, or no known binding to heparan sulfate. In some instances, having no affinity for heparan sulfate includes having no predicted binding affinity for heparan sulfate.

II. Detailed Description of Embodiments

A. Binding of Bacterial Pathogens by Convection Transport

The binding of bacterial pathogens to the essentially nonporous adsorption substrate of the present invention during convection transport is particularly effective under the relatively high-flow conditions typically employed in the safe operation of extracorporeal blood circuits, e.g. when measured by linear flow velocity, >8 cm/min, preferably about >30 cm/min, and more preferably about 30-1,000 cm/min.

In some embodiments, the adsorption media removes pathogens from whole blood in extracorporeal circuits with a linear flow rate of about 8 cm/min to about 1,000 cm/min, e.g., about 8 cm/min to about 30 cm/min, about 25 cm/min to about 100 cm/min, about 50 cm/min to about 200 cm/min, about 100 cm/min to about 1000 cm/min, about 200 cm/min to about 1000 cm/min, about 400 cm/min to about 1000 cm/min, about 500 cm/min to about 1000 cm/min, about 600 cm/min to about 1000 cm/min, about 100 cm/min to about 500 cm/min or about 300 cm/min to about 800 cm/min. In certain instances, the flow rate is about 10, 15, 20, 25, 30, 35, 40, 45, 50, 55, 60, 65, 70, 75, 80, 85, 90, 95 100 cm/min or about 25-40 cm/min.

In other embodiments, the adsorption media removes pathogens from whole blood in extracorporeal circuits with a volumetric flow rate, around 50 mL/minute to about 5 L/minute, e.g., 50 mL/min, 100 mL/min, 150 mL/min, 200 mL/min, 250 mL/min, 300 mL/min, 350 mL/min, 400 mL/min, 500 mL/min, 550 mL/min, 600 mL/min, 650 mL/min, 700 mL/min, 750 mL/min, 800 mL/min, 850 mL/min, 900 mL/min, 950 mL/min, 1.0 L/min, 1.5 L/min, 2.0 L/min, 2.5 L/min, 3.0 L/min, 3.5 L/min, 4.0 L/min, 4.5 L/min, and 5 L/min. In some embodiments, the flow rate is preferably >150 mL/minute.

Highly porous adsorbent media, in contrast, requires much lower flow rates of less than 1 mL/minute to about less than 50 mL/minute. Additionally, the residence time on the adsorption substrate (e.g., amount of time the adsorbate (e.g., bacteria) is in contact with the adsorbent media) needs to be much longer for a media requiring diffusive transport of adsorbates to the adsorbent site within the media, compared to a media using forced convection of adsorbates to the binding sites, which are not compatible with standard extracorporeal blood systems.

Typically, it is recognized that "residence time" on the adsorption column needs to be longer for a media requiring diffusive transport of adsorbates to the adsorbent site within the media, when compared to the lower residence time needed to convey an adsorbate to the binding site (on an essentially nonporous media) by forced convection. However, there are practical limits to the dimensions of a safe and effective adsorbent cartridge, column, filter, etc., especially with respect to the maximum hold-up volume of blood it can contain, and the flow velocity of blood or serum past the adsorption media. For this reason average flow rate through the adsorption device is considered to be a design variable.

Substrates that rely on forced convection transport are generally more suitable for high-flow rates, while substrates that rely on the much slower diffusion transport are much less effective when high flow rates and shorter residence times are required. For this reason, in an extracorporeal blood purification device, it is preferred that an adsorbate quickly diffuses through the pores within the adsorbent media. When blood is pumped through circuits fabricated from man-made materials, it is a general practice to employ relatively high blood flow rates in order to prevent stagnation and reduce the risk of clotting. On the other hand, extremely high flow rates may be avoided because they can expose blood cells to high shear rates and impingement damage that can rupture or otherwise damage blood cells. The present invention, therefore, provides a method and device for removing bacterial pathogens from blood using the preferred characteristics of convection transport and its desirable, more-rapid kinetics. This is achieved by passing/flowing blood over an essentially non-microporous substrate (e.g., a solid substrate), which is capable of binding the desired cytokine, pathogen or bacteria to remove them from the blood.

Adsorption media provided herein can be used in traditional extracorporeal blood circulation with flow rates >50 mL/min, and preferably between about 150 mL/minute to 5 L/minute. If measured by linear flow velocity, >8 cm/min, preferably about >24 cm/min and more preferably about 24-329 cm/min, or more. For example, the flow rate can be 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800 cm/min or more. Such high flow rates create short residence times within the adsorption column and convection transport dominates over Brownian diffusive transport. This is particularly important for binding larger particles such as viruses, bacteria and parasites and other proteins and pathogens that diffuse slowly.

The main adsorption sites available for removing bacterial pathogens lie at the surfaces within the interstices of the media bed, container or cartridge through which the blood flows or is delivered by forced convection. To treat blood, the interstitial channels need to be large enough to allow the transport of red blood cells, which are an average 6 microns in diameter. To allow a packed adsorption cartridge to be placed into an extracorporeal circuit with high blood flow rate, the interstitial channels can be several times larger than the diameter of red blood cells. This can prevent or substantially eliminate high shear rates that lead to hemolysis while simultaneously minimizing pressure drop in the blood that flows through the packed bed or cartridge. Additionally, the media is preferably rigid to minimize deformation that can clog the filter cartridge by compaction. Based on these preferences, an optimized rigid media balances interstitial channel size and total surface area, e.g., for efficient removal of pathogens and/or cytokines in high-flow extracorporeal blood circuits.

The claimed methods are intended to be applied primarily in extracorporeal therapies or procedures, and also implantable devices.

Whole blood and blood serum from mammals can be used in the present invention. The amount of blood or blood serum that can be used in the claimed methods is not intended to be limited. It can range from less than 1 mL to above 1 L, up to and including the entire blood volume of a patient or subject when continuous recirculation back to the patient is employed. One or more passes through the adsorption bed may be used if needed. The blood may be human or animal blood.

In some embodiments, bacteria or pathogens in the sample, e.g., whole blood or blood serum, is reduced by about 20% to about 90%, e.g., about 20%, 30%, 40%, 50%, 60%, 70%, 80%, 90% or 99.9%. In other embodiments, bacteria in the sample is reduced by about 20% to about 40%, e.g., about 20%, 25%, 30%, 35%, or 40% or about 5, 10, 15, 20, 25, 30, 35, 40, 45, 50, 55, 60, 65, 70, 75, 80, 85, 90, 95 or 99.9% reduction of the bacteria or pathogen.

In some embodiments, the bacteria in the sample is a gram-negative bacteria, such as any bacteria that does not retain crystal violet dye. Non-limiting examples of a gram-negative bacteria are *Klebsiella pneumoniae, Acinetobacter baumannii, Pseudomonas aeruginosa, Escherichia coli, Salmonella, Shigella, Stenotrophomonas maltophilia, Moraxella, Borrelia, Burkolderia, Campylobacter, Chlamydia, Hemophilus, Helicobacter, Stenotrophomonas, Vibrio, Leginella*, other Enterobacteriaceae, and drug-resistant strains thereof. In other embodiments, the bacteria in the sample is a gram-positive bacteria, such as any bacteria that retains crystal violet dye. Non-limiting examples of a gram-positive bacteria are *Actinomyces, Bacillus, Enterococcus, Lactobacillus, Listeria monocytogenes, Mycobacterium, Nocardia, Propionibacteriaum, Staphylococcus aureus, Staphylococcus epidermidis, Staphylococcus saprophyticus, Streptomyces, Streptococcus pneumoniae, Streptococcus pyrogenes, Streptococcus viridans*, Enterococci, *Clostridium difficile, Enterococcus faecium, Enterococcus faecalis*, and drug-resistant strains thereof.

In some embodiments, the methods provided herein are used to remove gram-negative bacteria from a whole blood or blood serum sample. In other embodiments, the methods are used to remove gram-positive bacteria from the sample. In yet other embodiments, the adsorption media described herein having a polysaccharide absorbant on its surface is used to remove bacteria such as *Escherichia coli, Klebsiella pneumoniae, Acinetobacter baumannii, Enterococcus faecium*, carbapenem-resistant *Escherichia coli*, carbapenem-resistant *Klebsiella pneumoniae*, and/or extended spectrum beta-lactamase *Klebsiella pneumonia* from the sample.

In some embodiments, the absorption media having a neutrally charged hydrophilic surface is used to remove *Staphylococcus aureus*, methicillin-resistant *Staphylococcus aureus* (MRSA), and/or *Escherichia coli* from a whole blood or blood serum sample. In other embodiments, the adsorption media having a cationic surface (hydrophilic surface) is used to remove *Escherichia coli, Klebsiella pneumoniae*, carbapenem-resistant *Escherichia coli*, carbapenem-resistant *Klebsiella pneumoniae*, and extended spectrum beta-lactamase *Klebsiella pneumoniae, Enterococcus faecium, Acinetobacter baumannii*, and methicillin-resistant *Staphylococcus aureus* (MRSA) from the sample.

B. Adsorption Media

Various materials, in shape and composition, can be used as a substrate in the present invention. All suitable adsorbent substrates provide high surface area while promoting the conveyance of adsorbates to the adsorbent sites that bind them (primarily) by forced convective transport. Useful substrates for creating the adsorption media include nonporous rigid beads, particles, or packing, reticulated foams, a rigid monolithic bed (e.g. formed from sintered beads or particles), a column packed with woven or non-woven fabric, a column packed with a yarn or solid or hollow non-microporous monofilament fibers, a spiral wound cartridge formed from flat film or dense membrane, or a combination of media such as a mixed bead/fabric cartridge. In some embodiments, a suitable substrate for use in the present invention is one that is initially microporous, but becomes essentially non-porous when the surface is treated before, during or after the creation of adsorption sites.

One useful substrate is in the form of solid beads or particles. The beads can be made of materials that are sufficiently rigid to resist deformation or compaction under the encountered flow rates. In some embodiments, sufficient substrate rigidity is the absence of a significant increase in pressure drop across the adsorption bed during about one hour of flow of water or saline at typical clinical flow rates. For instance, a suitable substrate rigidity is a <10-50% increase in pressure drop relative to the initial pressure drop (e.g., measured within the first minute of flow) when measured at a similar flow rate, e.g., of saline.

The adsorbent substrate beads may be made from a number of different biocompatible materials, such as natural or synthetic polymers or non-polymeric materials including glasses, ceramics and metals, that are essentially free of leachable impurities. Some exemplary polymers including polyurethane, polymethylmethacrylate, polyethylene or co-polymers of ethylene and other monomers, polyethylene imine, polypropylene, and polyisobutylene. Examples of useful substrates include nonporous Ultra High Molecular Weight PolyEthylene (UHMWPE). Other suitable beads are polystyrene, high density and low density polyethylene, silica, polyurethane, and chitosan.

The substrate such as beads, fiber, yarn and the like can be prepared with a surface roughness or topography to increase the adsorption surface area. For example, it is possible to increase the surface area by increasing the surface area to volume ratio. As is shown in FIG. 1A, an uneven and unulating surface produces more binding sites for the bacteria and pathogens. Typically a free form, shape, or geometry produces more surface area and is advantageous. FIG. 1A shows UHMWPE beads as received out of a reactor.

Methods for making beads are known in the art. For instance, suitable polyethylene beads and other polyolefin beads are produced directly during the synthesis process. In some instances, the beads are processed to the required size and shape. Other polymers may need to be ground or spray dried and classified, or otherwise processed to create beads of the desired size distribution and shape.

In some aspects, the adsorption media of the present invention provides a surface to attach a polysaccharide adsorbent that can bind a bacterial pathogen. In some embodiments, the adsorption media includes a solid substrate with a high surface area having at least one polysaccharide adsorbent on the surface thereof.

In other aspects, an adsorption media of the present invention provides a hydrophilic surface without a polysaccharide adsorbent ("a naked surface"). In some embodiments, the adsorption media includes a solid substrate with a high surface area and a hydrophilic cationic surface. In other embodiments, the adsorption media includes a solid substrate with a high surface area and a hydrophilic neutral surface.

The solid substrate can be made of, for example, but not limited to, polyethylene, polystyrene, polypropylene, polysulfone, polyacrylonitrile, polycarbonate, polyurethane, silica, latex, glass, cellulose, crosslinked agarose, chitin, chitosan, crosslinked dextran, crosslinked alginate, silicone, fluoropolymer, and other synthetic polymers. The solid substrate with a high surface area can be a plurality of adsorbent monolayers, filters, membranes, solid fibers, hollow fibers, particles, or beads. Optionally, the solid substrate can be present in other forms or shapes providing a large surface area.

In certain instances, the solid substrate is a plurality of rigid polymer beads such as polyethylene, polystyrene, polypropylene, polysulfone, polyacrylonitrile, polycarbonate, polyurethane, silica, latex, glass, cellulose, crosslinked agarose, chitin, chitosan, crosslinked dextran, crosslinked alginate, silicone, fluoropolymer, and synthetic polymer beads. Preferably, the rigid polymer beads are polyethylene beads.

The size of the solid substrate can be selected according to the volume of the test sample used in the assay or other parameters. In some embodiments, each bead of the plurality of rigid polymer beads has an average outer diameter of about 1 µm to about 1 mm, e.g., 1 µm, 2 µm, 3 µm, 4 µm, 5 µm, 6 µm, 7 µm, 8 µm, 9 µm, 10 µm, 15 µm, 20 µm, 25 µm, 30 µm, 35 µm, 45 µm, 55 µm, 60 µm, 65 µm, 70 µm, 75 µm, 80 µm, 85 µm, 90 µm, 95 µm, 100 µm, 200 µm, 300 µm, 400 µm, 500 µm, 600 µm, 700 µm, 800 µm, 900 µm, or 1 mm. In other embodiments, the each bead of the plurality of rigid polymer beads has an average diameter of about 10 µm to about 200 µm, e.g., 10 µm, 15 µm, 20 µm, 25 µm, 30 µm, 35 µm, 45 µm, 55 µm, 60 µm, 65 µm, 70 µm, 75 µm, 80 µm, 85 µm, 90 µm, 95 µm, 100 µm, 105 µm, 110 µm, 115 µm, 120 µm, 125 µm, 130 µm, 135 µm, 140 µm, 145 µm, 150 µm, 155 µm, 160 µm, 165 µm, 170 µm, 175 µm, 180 µm, 185 µm, 190 µm 195 µm, or 200 µm.

In some embodiments, useful beads have a size ranging from about 100 microns (µm) to 500 µm, or more in diameter, e.g., 100 µm, 150 µm, 200 µm, 250 µm, 300 µm, 350 µm, 400 µm, 450 µm, 500 µm, or more, in diameter. The average size of the beads can be from about 150 µm to about 450 µm in diameter, e.g., 150 µm, 200 µm, 250 µm, 300 µm, 350 µm, 400 µm, or 450 µm in diameter. For example, polyethylene beads from Polymer Technology Group (Berkeley, Calif.) having an average diameter of 300 µm are suitable for the present invention.

In some embodiments, the substrate is a barrier membrane, e.g., a non-porous film. Alternatively, a microporous membrane may be rendered non-porous by filling the pores with essentially non-porous material, e.g., a polymer. The membrane in the form of a sheet or a solid or hollow fiber may be arranged within a housing or a container.

The adsorption media can be in a vessel such as a column, cartridge, tube, centrifuge tube, bed, and the like, or any vessel wherein the cells of the blood that are not captured onto polysaccharide bound adsorption media can be removed without disturbing the bacterial pathogen attached to the media.

The substrate is typically provided packed within a housing or container, such as a column, that is designed to hold the substrate within the container and permit the blood or serum to flow over the surface of the substrate or bed. The substrate may be arranged within the container to maximize the binding of the adsorbates to the absorbent sides of the substrate. The housing or container can have a macroporous surface structure that provides a large surface area to the blood or serum.

A column or other housing shape can be packed with either woven or non-woven heparinized fabric or the heparin, heparan sulphate or optional non-heparin adsorption sites may be attached, e.g. by covalent, ionic or other chemical or physical bonds, after the housing has been filled with the substrate media. By controlling the fiber denier and density of the fabric during weaving or knitting or during the creation of a non-woven web, the interstitial pore size can be controlled. Useful non-woven fabrics may be in the form of felts, melt-blown, or electrostatically spun webs, having a random orientation held together by entanglement of the fibers and/or adhesion or cohesion of intersecting fibers. Useful woven fabrics have a more defined and non-random structure.

A column or housing can be packed with fibers or yarns made from fibers. Polyethylene, and other fibers, can be drawn into thin hollow or solid monofilament fibers or multifilament yarns, which can be packed into cartridges in the same way that hollow fiber membranes, are installed within conventional hemodialysis cartridges or blood oxygenators. In the present invention, originally porous hollow fibers are rendered dense or non-porous before, during or after binding heparin or other adsorbents to the outer and/or inner surfaces. Dyneema Purity® from Royal DSM is a high-strength solid fiber made of UHMWPE. Ultra-high-molecular-weight polyethylene (UHMWPE, UHMW) is a subset of the thermoplastic polyethylene. Dyneema can be heparinized and packed into a cartridge to provide a high-surface area support for the removal of cytokines, bacteria and pathogens.

A spiral wound cartridge contains a thin film or membrane that is tightly wound together with optional spacer materials to prevent contact of adjacent surfaces. The membrane can be made from polymers such as polyurethane, polyethylene polypropylene, polysulfone, polycarbonate, PET, PBT, and the like.

As noted above, in certain instances, for use in the methods of the invention, the size of the channels or interstitial space between individual beads for extracorporeal blood filtration are optimized to prevent a high-pressure drop between the inlet and outlet of the cartridge, to permit safe passage of the blood cells between the individual beads in a high flow environment, and to provide appropriate interstitial surface area for binding of the polysaccharide adsorbent to the cytokines or pathogens in the blood. For example, in a close packed bed of 300-micron, roughly spherical beads, an appropriate interstitial pore size is approximately 68 microns in diameter.

In some embodiments, the rigid beads of the adsorption media have an average diameter as is listed in Table 5. In some embodiments, the non-bead substrates of the adsorption media such as woven yarns or fibers have a macroscopic pore size as set forth in Table 6.

C. Methods for Making Adsorption Media

The surface of the solid substrate described herein can be functionalized to allow the covalent attachment of the polysaccharide adsorbent described herein. In some embodiments, the surface of the solid substrate has at least one chemical group, such as an amine group.

Polysaccharides such as heparin or heparan sulfate or other polysaccharides can be linked onto the surface of the adsorption media by covalent end-point attachment (e.g., covalent attachment through the terminal residue of the heparin molecule). Covalent attachment as compared to non-covalent attachment advantageously provides better control of the orientation of the immobilized molecules and their surface density. In particular, the end-point attachment of these long chain carbohydrates provides a spacer function that leads to a higher concentration of accessible carbohydrate oligomers available for pathogen binding. In fact, certain pathogens attach to full-length heparin (e.g., heparin with a mean molecular weight of more than 10 kDa) coated surfaces much more efficiently than to conventional surfaces coated with heparin fragments, as is generally employed in the art.

In some embodiments, the immobilized full-length heparin molecules have a mean molecular weight of more than 10 kDa. In other embodiments, the immobilized heparin molecules have a mean molecular weight of more than 15 kDa. In another embodiment, the immobilized heparin molecules have a mean molecular weight of more than 21 kDa. In yet another embodiment, the immobilized heparin molecules have a mean molecular weight of more than 30 kDa. Preferably, the immobilized heparin molecules have a mean molecular weight within the range of 15-25 kDa. The mean molecular weight may also be higher, such as in the range of 25-35 kDa.

In some embodiments, the surface concentration of the heparin adsorbent on the solid substrate is in the range of 1 $\mu g/cm^2$ to 20 $\mu g/cm^2$, e.g., 1 $\mu g/cm^2$, 2 $\mu g/cm^2$, 3 $\mu g/cm^2$, 4 $\mu g/cm^2$, 5 $\mu g/cm^2$, 6 $\mu g/cm^2$, 7 $\mu g/cm^2$, 8 $\mu g/cm^2$, 9 $\mu g/cm^2$, 10 $\mu g/cm^2$, 11 $\mu g/cm^2$, 12 $\mu g/cm^2$, 13 $\mu g/cm^2$, 14 $\mu g/cm^2$, 15 $\mu g/cm^2$, 16 $\mu g/cm^2$, 17 $\mu g/cm^2$, 18 $\mu g/cm^2$, 19 $\mu g/cm^2$, and 20 $\mu g/cm^2$. In other embodiments, the surface concentration of the heparan adsorbent on the solid substrate is in the range of 5 $\mu g/cm^2$ to 15 $\mu g/cm^2$, e.g., 5 $\mu g/cm^2$, 6 $\mu g/cm^2$, 7 $\mu g/cm^2$, 8 $\mu g/cm^2$, 9 $\mu g/cm^2$, 10 $\mu g/cm^2$, 11 $\mu g/cm^2$, 12 $\mu g/cm^2$, 13 $\mu g/cm^2$, 14 $\mu g/cm^2$, and 15 $\mu g/cm^2$.

The amount of polysaccharide adsorbent per gram substrate can vary. In one particular embodiment, if beads are used, the amount of polysaccharide, such as heparin per gram bead is determined by the number of layers used and also the size of the beads. The larger the bead, the less polysaccharide, such as heparin per gram of bead is achieved. One preferred amount is 2.0±0.5 mg heparin/g bead per the MBTH method (Larm et al., *Biomater Med Devices Artif Organs*, 1983, 11:161-173 and Riesenfeld and Rosen, *Anal Biochem*, 1990, 188:383-389).

Covalent attachment of full-length heparin molecules to a surface can be achieved by the reaction of an aldehyde group of the heparin molecule with a primary amino group present on the surface of the adsorption media. An inherent property of all carbohydrates is that they have a hemiacetal in their reducing end. This acetal is in equilibrium with the aldehyde form and can form Schiffs bases with primary amines. These Schiffs bases may then be reduced to stable secondary amines. In some embodiments, full-length heparin is surface immobilized onto the solid substrate by covalent conjugation. In other embodiments, full-length heparin is covalently attached to said adsorption media via a stable secondary amino group.

In certain instances, various methods of making adsorbents and the adsorbents per se are disclosed in U.S. Pat. No. 8,663,148 and U.S. Patent App. Publication Nos. US2009/0136586, US2010/0249689, US2011/0184377, and US2012/0305482, the disclosures of which are herein incorporated by reference in their entirety for all purposes.

In some embodiments, the adsorption media is hydrophilized prior to attachment of the polysaccharide, such as heparin, or other compounds. Methods for preparing the hydrophilic surface of the substrate include acid etching, plasma treating, and exposure to strong oxidizers. For instance, a polymeric surface such as a polyethylene (PE) bead can be etched with an oxidizing agent, such as potassium permanganate, ammonium peroxidisulfate and the like, to introduce hydrophilic properties together with some reactive functional groups (e.g., a sulfonyl group, a hydroxyl group, a carboxyl group, a carbonyl group, or carbon double bonds). The surface can be etched with plasma or corona. For example, PE beads can be etched with an potassium permanganate in sulfuric acid to produce beads with a hydrophilic surface containing hydroxyl groups and carbon double bonds.

D. Mixtures of Adsorption Media

In certain instances, the methods of the invention prepares the adsorption bed from a mixture of heparinized media which is antithrombogenic and another media which is inherently thrombogenic. By assembling an adsorption cartridge with both heparinized surfaces and, for example, hydrophilic surfaces (cationic or neutral surfaces), bacterial pathogens can all be safely removed from blood or other biological fluid. For example, the heparinized media can be from 1% to 99% of the adsorption bed and the and the inherently thrombogenic substrate can be from 99% to 1% of the adsorption bed.

In some embodiments of the present invention, the adsorption media provides an antithrombogenic surface that is in intimate contact with, or in close proximity to a thrombogenic surface. This adsorption media can prevent clinically significant thrombus formation that would otherwise occur if the inherently thrombogenic surface were used alone.

In the case of adsorption media in the form beads or particles, a preferred application of this invention is to blend the different adsorption media together before packing them into a cartridge or other housing. This provides intimate contact among the various surface chemistries on adjacent beads while permitting efficient manufacturing of adsorption cartridges or filters. A related approach is to layer the different media in a 'parfait-type' arrangement within the housing such that the blood contacts the different media in series or parallel flow. One arrangement of the different media within a cartridge is to position unblended antithrombogenic media at the entrance and/or the exit of the cartridge, with an optionally blended region containing the more thrombogenic media interposed between the entrance and exit regions.

In the case of media in fiber form, a mixed woven, knitted, or nonwoven structure can be prepared by methods well known in the textile industry to form fabric from the mixed fiber. Alternatively, a yarn can be prepared from finer multifilament yarn or monofilament made from two or more fibers with different surface chemistries, as long as one fiber type contains a surface that actively prevents blood clotting on contact. The mixed-fiber yarn can then be used to prepare fabric for blood contact. Hollow fiber or solid fiber adsorption media can be blended and used to make cartridges that resemble hollow-fiber dialyzers or oxygenators. For membrane or film-type adsorption media of the type that is used in a spiral-wound adsorption cartridges, two or more surface chemistries may be used in close proximity to each other such that the blood must contact both surface chemistries (nearly) simultaneously. This can be done with a regular or random array of the various binding groups within the surface layer of the membrane film, or by forming a flow path for blood between two closely-spaced membrane films, one of which is antithrombogenic.

E. Extracorporeal Blood Filter

In certain aspects, methods provided herein can be used in a device comprising adsorption media for extracorporeal removal of pathogens from mammalian blood, e.g., human blood. For instance, the device can be a conventional device for extracorporeal treatment of blood and serum from patients, e.g. a subject suffering from renal failure.

Local blood flow patterns in blood contacting medical devices for extracorporeal circulation are known to influence clot formation via shear activation and aggregation of platelets in stagnant zones. The device containing the adsorption media provided herein may, for example, have one or more of the following properties: a) a blood flow in the range of 150-5,000 ml/min, or if measured by linear flow velocity of >8 cm/min; b) low flow resistance; c) large surface area of substrate having carbohydrates immobilized thereto, e.g. about 0.1-1 $m^2$; d) a stable coating (e.g., no clinically significant leakage of carbohydrate to the blood in contact therewith); e) proper hemodynamic properties in the device (e.g., no stagnant zones); and f) optimal biocompatibility.

Non-limiting examples of a device for use according to the methods of the present invention include an extracorporeal membrane oxygenation (ECMO) device, a pediatric hemoflow dialyzer which is an extracorporeal blood filtration device for removing cytokine molecules or other extracorporeal device that can accommodate high flow rates.

The methods of the present invention can be employed either before or after other conventional treatments, such as administration of antibiotics.

In some embodiments, the methods are performed in a continuous loop such that, the sample, e.g., whole blood, is extracted from the body and processed according to the method provided herein, and then the resulting sample (e.g., sample containing a reduced amount of bacterial pathogen) is reintroduced into the body, thereby forming a loop comprising part of the bloodstream of the patient.

In other embodiments, the methods provided herein can be combined with other techniques to filter or treat mammalian blood. For example, a cartridge that is based on convection kinetics can then be used in series with conventional extracorporeal circuits such as cardiopulmonary bypass (CPB), hemodialysis, extracorporeal blood oxygenation and ozonation (EBOO), and the like.

The various aspects of the invention are further described in the following examples. These examples are not intended to be limiting. For instance, in the present examples heparin is used. However, other carbohydrates and polysaccharide adsorbents may be used alone or in addition to the heparin-coated substrates exemplified below.

III. EXAMPLES

The following examples are offered to illustrate, but not to limit, the claimed invention.

Example 1. Removal of Bacteria with Low or Undetectable Affinity for Heparan Sulfate This example illustrates the use of heparin coated beads to remove bacterial pathogens with low affinity or undetectable affinity for heparan sulfate from whole blood.

It has been reported in the literature that over 50 different pathogens target heparan sulfate proteoglycans found on syndecans as an initial attachment site during their pathogenesis. Surprisingly, surface bound heparin can function as a surrogate to heparan sulfate binding organisms.

Our studies have shown that heparinized adsorption media can remove high concentration of *S. aureus* and MRSA from whole blood. Also, the study showed that the bacteria attached to the heparinized surface were not killed, and thus did not release potential inflammatory toxins and their byproducts into the blood. Thus, the heparin-bound media can be used in an extracorporeal device to effectively and safely remove circulating bacteria including drug-resistant strains from infected blood.

This example tests both known heparan sulfate binding pathogens and pathogens either unknown or unexpected to bind to heparin. Additionally, it was discovered that hydrophilic controls, either cationic or neutrally charged, can function as an effective surface to bind pathogens. Neutrally charged surfaces in general were not as effective as heparinized surfaces in removing pathogens, but it is feasible that a pathogen reduction technology could be developed using generic hydrophilic surfaces. Hydrophilic cationic surfaces showed reasonable ability to remove pathogens as well.

This example illustrates that an adsorption media comprising a surface-bound heparin can be used to remove expected heparan sulfate binding pathogens such as, *S. aureus*, methicillin-resistant *S. aureus* (MRSA), *E. faecalis*, vancomycin-resistant *E. faecalis*, HSV-1 and HSV-2, and *Candida albicans*.

This example illustrates that an adsorption media comprising a surface-bound heparin can be used to remove low (e.g., zero) affinity heparan sulfate-binding pathogens, such as, *E. coli*, carbapenem-resistant *E. coli*, *K. pneumoniae*, carbapenem-resistant *K. pneumoniae*, extended spectrum beta-lactamase *K. pneumoniae*, *E. faecium*, *A. baumannii*, and *S. pneumonia*, from blood.

In particular, an adsorption media comprising a neutral hydrophilic surface can remove, for example, *S. aureus*, methicillin-resistant *S. aureus* (MRSA), and *E. coli*. Also, an adsorption media comprising a cationic hydrophilic surface can remove, for example, *E. coli*, *K. pneumoniae*, carbapenem-resistant *K. pneumoniae*, extended spectrum beta-lactamase *K pneumoniae*, *E. faecium*, *A. baumannii*, and methicillin-resistant *S. aureus* (MRSA).

*S. aureus* or methicillin-resistant *S. aureus* (MRSA) bacteremia exhibit a natural affinity towards heparin and heparin sulfate (HS). An affinity adsorption technology has been developed that relies on this natural mechanism to remove bacteria from blood. The primary ligand is end-point attached heparin, an analogue of heparan sulfate. Not only does the heparin provide the mechanism of action to remove bacteria from whole blood, it also provides an anti-thrombogenic surface that enhances the safety of the extracorporeal circuit.

The targeting of carbohydrates and proteoglycans for initial attachment is a common mechanism of most pathogens. For instance, influenza viruses will bind to sialic acid, a carbohydrate found in many glycoproteins. Many gram negative bacteria have mannose binding adhesins located on the tips of fimbriae. Other carbohydrates that have shown to be targeted by bacteria include L-fucose, galactose, and various glucosamines or galactoamines. The common theme of pathogens binding to carbohydrates is the ubiquitous nature of the glycocalyx on cell surfaces.

The bacteria that have been targeted in this example include *E. coli*, *Klebsiella pneumoniae*, and their carbapenem-resistant strains, and also *P. aeruginosa*. There are many different adhesins reported for gram negative bacteria. The most studied are Fimbriae of Type 1, Type 3, Type P, and Type S and also outer membrane protein A (OmpA). Type 1 fimbriae and OmpA have been implicated in the attachment to endothelial cells. Type 1 fimbriae mediate attachment to mannose (mannose-sensitive) and are expressed in the majority of Enterobacteriacea. Other fimbriae have adhesins for different carbohydrates and are considered mannose-resistant. Typically, several types of fimbriae are expressed simultaneously.

In addition, it has been shown that mannose-sensitive adhesins are present on the bacterial cell surface even when fimbriae are not expressed. Type 1 fimbriae have been shown to interact with human brain microvascular endothelial cells suggesting that fimbriae can be expressed in blood. Drug resistant strains of *Klebsiella pneumoniae* express a higher concentration of both Type 1 and Type 3 fimbriae.

A heparinized surface to target removal of *S. aureus*, MRSA, *S. pneumoniae*, *E. faecalis*, *E. faecium*, herpes simplex virus, specific exotoxins, and other HS targeting pathogens was investigated. In vitro studies have confirmed the affinity of many of these pathogens and toxins for heparinized media.

The second adsorption media developed was a mannose functionalized surface to target gram negative bacteria, such as *E. coli*, *K. pneumoniae*, and *A. baumannii*. In vitro studies confirmed that mannose media can bind these pathogens. It was demonstrated that MRSA had no affinity to the mannose media. However, the heparinized media was also very effective at removing these gram negative bacteria that were not expected to have a high affinity for heparin. These results were unexpected, and therefore it is not possible to predict based on literature alone which bacteria can be removed from blood by a heparinized surface.

Results

A. Results

The first report of successful removal of bacteria from whole blood was published in 2011 (Mattsby-Baltzer et al., *J. Microbiol. Biotechnol.*, 2011, 21(6), 659-664). In this study, it was shown that a high concentrations of *S. aureus* and MRSA were removed from whole blood using the heparinized media. In addition, it was demonstrated using PCR that the bacteria were not killed when they attach to the heparinized surface and therefore did not release potential inflammatory toxins/byproducts into the bloodstream. The use of the heparinized media creates a very broad spectrum device that can safely remove circulating bacteria from blood, regardless of drug resistance.

The heparin adsorption media does not function by adding any detectable chemical substances to the treated blood or blood products. Instead it uses (non-leaching) covalently-bound, end-point-attached heparin as a ligand in a rapid adsorption process not limited by diffusion.

As discussed herein, *S. aureus* and MRSA can be removed from whole blood using the heparinized media. Several strains of *S. aureus* and MRSA were tested in this study. The results are shown in Table 1. *S. aureus* and several strains of MRSA were removed in high yield from whole blood. Depending on the strain, up to 85% of MRSA bacteria were removed by the heparinized media.

TABLE 1

Removal of *S. Aureus* and MRSA Strains From Whole Blood
*S. Aureus* and MRSA Strains tested

|  | SA1800T | MRSA485 | MRSA251 | MRSA860 |
|---|---|---|---|---|
| % Removed in one pass | 62% | 85% | 59% | 70% |

In an in vitro blood study, 85% of MRSA was removed by a single pass through the media (Table 2).

TABLE 2

Removal of both drug susceptible and drug resistant pathogens

| Bacteria | % Reduction | Capacity (CFU/g) |
| --- | --- | --- |
| Gram Positive Bacteria | | |
| MRSA | 91.57% | 3.69E+05 |
| S. pneumoniae | 53.06% | 1.73E+05 |
| E. faecalis | 99.04% | 2.12E+06 |
| E. faecalis(VRE) | 91.25% | 1.88E+06 |
| E. faecium | 56.38% | 1.72E+06 |

The starting concentration of bacteria was $5 \times 10^6$ CFU/mL. In addition to binding MRSA, PCR analysis indicated that the heparinized surface was not bactericidal. This is an important finding that indicates cellular components of (dead) bacteria, which can be inflammatory and toxic to the recipient, are not released into the blood when bacteria attach to the media.

Additional studies were performed to test the affinitiy of various pathogens for the heparinized media. In these studies, 2.5 ml filter syringes were filled with heparinized media or control media to test the removal of various gram negative and gram positive bacteria. The bacteria were cultured using standard methods and diluted in defibrinated horse blood. The blood was then passed over the saline rinsed media a total of 3 times, and then plated for CFU counts. The targeted CFU/ml concentration was typical for antimicrobial testing and ranged between $10^5$ and $10^6$ CFU/ml.

A summary table reporting the removal of pathogens using the heparinized media is shown in Table 2.

B. Unexpected Results

Several pathogens reported in the literature with either little, no affinity, or unknown affinity to heparin or heparin sulfate were tested using the same protocols used for the heparin bind pathogens. Table 3 lists these bacteria and the results. Surprisingly, many gram negative bacteria and their drug resistant strains were removed in high concentration from blood.

TABLE 3

Unexpected removal of gram negative
bacteria using a heparinized surface

| Gram Negative Bacteria | % Reduction | Capacity (CFU/g) |
| --- | --- | --- |
| K. pneumoniae (CRE) | 99.94% | 4.66E+05 |
| K. pneumoniae | 36.57% | 4.90E+05 |
| E. coli (CRE) | 99.93% | 8.56E+05 |
| E. coli | 99.75% | 2.04E+06 |
| A. baumannii | 79.13% | 4.83E+05 |

Conclusion

The results show that heparinized media has an extremely high capacity to remove a broad spectrum of bacteria from blood. Unexpectedly, several bacteria with either no known affinity or had little affinity to heparin or heparin sulfate were also removed. Therefore, there is little predictability regarding the affinity that many pathogens may or may not have towards heparinized surface chemistry. The adsorption of several gram positive bacteria, including reported heparin binding pathogens, suggests that these pathogens bind specifically to the heparinized surface. Without being bound to any particular theory, it is believed that hydrophilic surfaces, such as neutral or cationic surfaces on the adsorption media, can be used to remove bacteria with no known affinity (or low affinity) to heparin or heparan sulfate. Alternatively, the binding of the above listed gram negative bacteria may be through interaction of specific sites or via non-specific binding. The surface topography of the adsorption media may be important to this binding.

Example 2. Adsorption Media with a Hydrophilic Surface

This example shows the adsorption media comprising a hydrophilic surface which can be used to removed bacteria from whole blood or serum.

The adsorption media described herein contains a surface topography that enables its binding to pathogens, such as those with no affinity or low affinity to heparin (FIG. 1A). Without being bound by any particular theory, it is believed that a rough, uneven or ungulating surface may contribute to the affinity of the bacteria to the adsorption media.

Figure 1B:
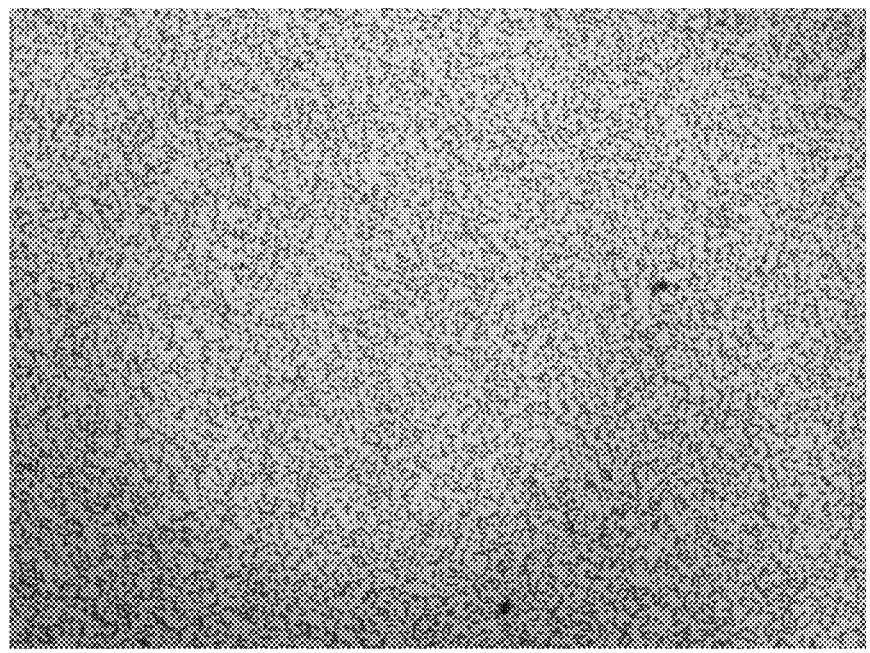
Figure 2:
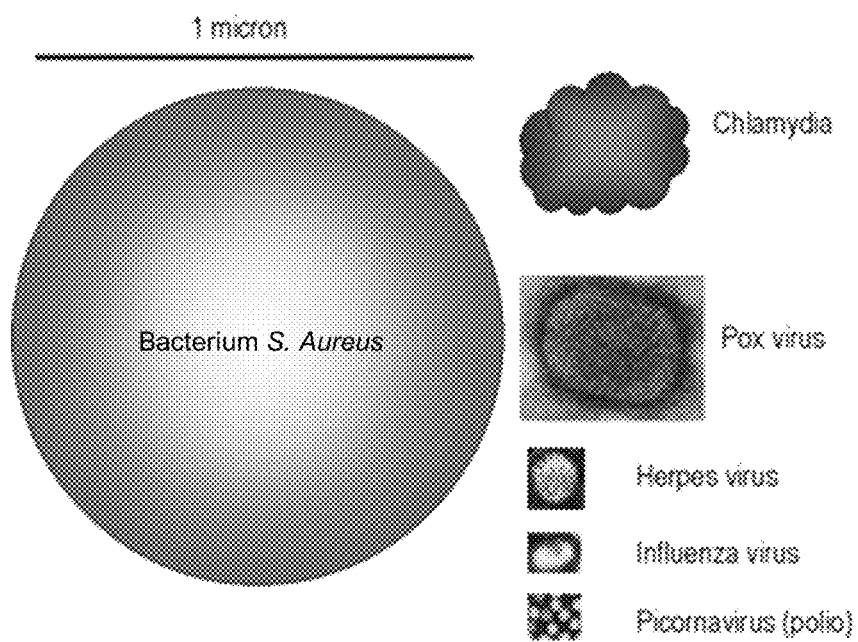
FIG. 2 shows a size comparison of bacteria, e.g., *Staphylococcus aureus* and *Chlamydia*, and viruses, e.g., pox virus, herpes virus, influenza virus, and picornavirus (polio).

FIG. 1B shows an image of a human blood smear for comparison. FIG. 2 shows a size comparison of bacteria, e.g., *Staphylococcus aureus* and *Chlamydia*, and viruses, e.g., pox virus, herpes virus, influenza virus, and picornavirus (polio).

Example 3. Blood Filters for Use in High Linear Flow Rate Extracorporeal Therapies This example provides an exemplary design of an extracorporeal filter cartridge that is used to accommodate high linear flow rates.

An extracorporeal blood filter can be designed to operate safely at specific flow rates used with common pump systems. If the pressure drop across a blood filter is too high, hemolysis can occur. Typically, dialysis systems operate with pressures below 34 kPa to avoid the risk of hemolysis.

For a cartridge filled with packed adsorbent media, the pressure drop across the cartridge depends on the flow rate, particle size, particle modulus, height of the packed media, and viscosity of blood. If a filter media is not sufficiently rigid, then compression of the media can occur with increased blood flow resulting in a reduced porosity that can lead to unsafe pressures.

The first variable to determine is the minimum particle size allowable for specific column heights and linear flow rates. Typical flow rates of dialysis systems are between 100 and 400 ml/min which equates to a linear flow rate of roughly 8 and 30 cm/min depending on the cartridge diameter. Typical volumetric flow rates of cardiopulmonary bypass (CPB) and extracorporeal membrane oxygenators (ECMO) can be up to 5000 ml/min. Thus, depending on the cartridge width, the linear flow rate could be as high as 1000 cm/min. If a cartridge is made wider, the linear flow rate can be decreased to reduce pressure.

In determining the minimum particle size based on linear flow rate and particle size, it is necessary not to exceed pressures that can cause hemolysis. The Blake-Kozeny equation describes the pressure drop across packed media of rigid solids.

$$\Delta P = \mu * \left(\frac{Ko}{d_p^2}\right) \frac{(1-\varepsilon)^2}{\varepsilon^2} L * u$$

where μ is the viscosity of blood; $K_o$ is a constant; $d_p$ is the diameter of the particle; E is the interstitial bed porosity or void volume; L is the height of the packed media; and u is the linear flow rate.

The equation can be solved for $d_p$ $$d_p = \sqrt{\frac{\mu * Ko}{\Delta P} * \frac{(1-\varepsilon)^2}{\varepsilon^2} L * u}$$

If 34 kPa is the maximum allowable pressure, then the following variables are used to determine particle size as a function of flow rate and column height.

$\mu = 4$ cp viscosity of blood $Ko = 150$ constant $\varepsilon = 0.36$ (can range from 0.3-0.5 depending on packing efficiency)

$\Delta P = 34$ kPa Maximum allowable pressure 255 mmHg 4.9 PSI $\frac{(1-\varepsilon)^2}{\varepsilon^2} = 8.78$ $\frac{\mu * Ko}{\Delta P} = 1.76E\text{-}05$ The minimum bead diameter for a given linear velocity and column height are given in Table 4.

TABLE 4

Low Volumetric Flow Rates
bead diameter (microns)

| | L (column height in cm) | | | | |
|---|---|---|---|---|---|
| u (cm/min) | 3 | 5 | 10 | 20 | 30 |
| 1 | 22 | 28 | 39 | 56 | 68 |
| 3 | 37 | 48 | 68 | 96 | 118 |
| 5 | 48 | 62 | 88 | 124 | 152 |
| 7 | 57 | 74 | 104 | 147 | 180 |
| 9 | 65 | 83 | 118 | 167 | 205 |
| 11 | 72 | 92 | 131 | 185 | 226 |
| 13 | 78 | 100 | 142 | 201 | 246 |

TABLE 4-continued

Low Volumetric Flow Rates
bead diameter (microns)

| | L (column height in cm) | | | | |
|---|---|---|---|---|---|
| u (cm/min) | 3 | 5 | 10 | 20 | 30 |
| 15 | 83 | 108 | 152 | 216 | 264 |
| 17 | 89 | 115 | 162 | 230 | 281 |
| 19 | 94 | 121 | 172 | 243 | 297 |
| 21 | 99 | 128 | 180 | 255 | 312 |
| 23 | 103 | 133 | 189 | 267 | 327 |
| 25 | 108 | 139 | 197 | 278 | 341 |
| 27 | 112 | 145 | 205 | 289 | 354 |
| 29 | 116 | 150 | 212 | 300 | 367 |
| 31 | 120 | 155 | 219 | 310 | 380 |

Figure 3:
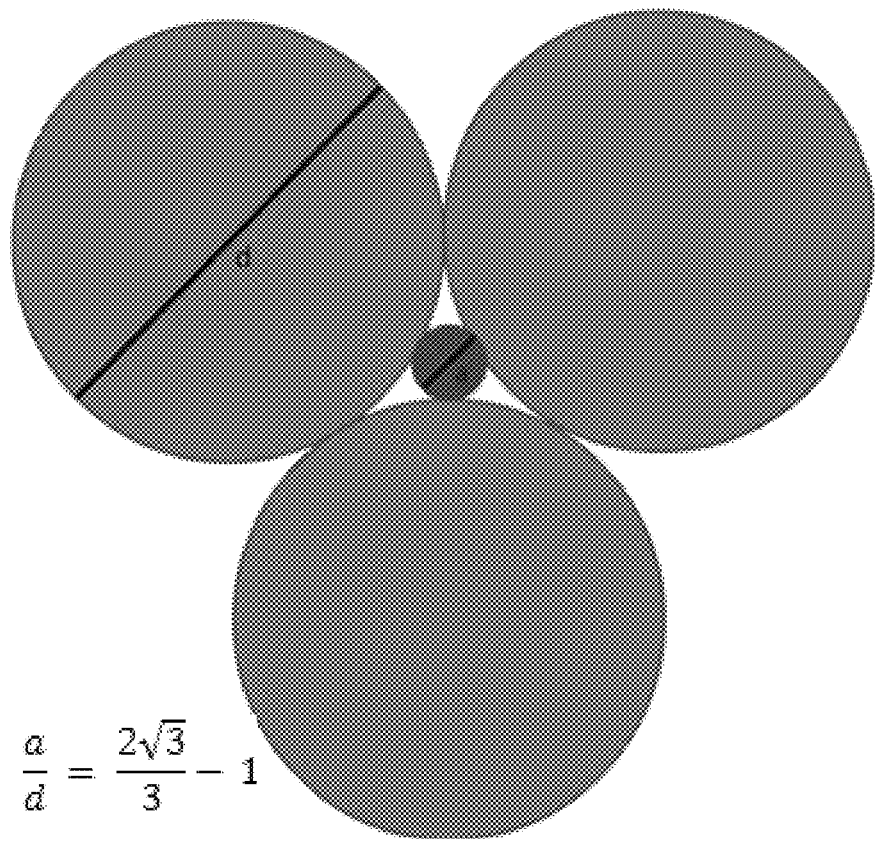
FIG. 3 illustrates a cross-section of the adsorption media containing beads with a diameter (d) and a cell with a diameter (a).

However, the size of blood cells can also be taken into account, as the effective pore size cannot be too small to block passage of blood cells. Macrophages are the largest cells in the blood and are about 21 microns, so it is important that these cells are allowed to pass through the filter media (FIG. 3).

The throat size represented by "a" in FIG. 3, i.e., the smallest opening between beads in a packed media, is described more fully below. The neck size can be calculated by the following equation.

$$a = d_p * \frac{2\sqrt{3}}{3} - 1$$

The minimum neck size must then be at least 21 microns. Therefore, the minimum bead size is:

$$d_{pmin} = \frac{a}{\frac{2\sqrt{3}}{3} - 1}$$

where $d_{pmin} = 136$ microns

Thus, the minimum size allowable is 136 microns. Table 5 represents useful linear flow rates and column heights for beads equal to or greater than 136 μm in diameter.

TABLE 5

Bead Size in Relation to Linear Flow and Column Height

| | bead diameter (microns) | | | | | | bead diameter (microns) | | | | |
|---|---|---|---|---|---|---|---|---|---|---|---|
| | L (column height in cm) | | | | | | L(column height in cm) | | | | |
| u (cm/min) | 3 | 5 | 10 | 20 | 30 | u (cm/mm) | 3 | 5 | 10 | 20 | 30 |
| 1 | 136 | 136 | 136 | 136 | 136 | 1 | 136 | 136 | 136 | 136 | 136 |
| 3 | 136 | 136 | 136 | 136 | 136 | 76 | 188 | 243 | 343 | 485 | 594 |
| 5 | 136 | 136 | 136 | 136 | 152 | 151 | 265 | 342 | 484 | 684 | 838 |
| 7 | 136 | 136 | 136 | 147 | 180 | 226 | 324 | 418 | 592 | 837 | 1025 |
| 9 | 136 | 136 | 136 | 167 | 205 | 301 | 374 | 483 | 683 | 966 | 1183 |
| 11 | 136 | 136 | 136 | 185 | 226 | 376 | 418 | 540 | 763 | 1079 | 1322 |
| 13 | 136 | 136 | 142 | 201 | 246 | 451 | 458 | 591 | 836 | 1182 | 1448 |
| 15 | 136 | 136 | 152 | 216 | 264 | 526 | 494 | 638 | 903 | 1277 | 1564 |
| 17 | 136 | 136 | 162 | 230 | 281 | 601 | 529 | 682 | 965 | 1365 | 1671 |
| 19 | 136 | 136 | 172 | 243 | 297 | 676 | 561 | 724 | 1023 | 1447 | 1773 |
| 21 | 136 | 136 | 180 | 255 | 312 | 751 | 591 | 763 | 1079 | 1525 | 1868 |
| 23 | 136 | 136 | 189 | 267 | 327 | 826 | 620 | 800 | 1131 | 1600 | 1959 |

TABLE 5-continued

Bead Size in Relation to Linear Flow and Column Height

| | bead diameter (microns) | | | | | | bead diameter (microns) | | | | |
|---|---|---|---|---|---|---|---|---|---|---|---|
| | L (column height in cm) | | | | | | L (column height in cm) | | | | |
| u (cm/min) | 3 | 5 | 10 | 20 | 30 | u (cm/mm) | 3 | 5 | 10 | 20 | 30 |
| 25 | 136 | 139 | 197 | 278 | 341 | 901 | 647 | 835 | 1181 | 1671 | 2046 |
| 27 | 136 | 145 | 205 | 289 | 354 | 976 | 674 | 870 | 1230 | 1739 | 2130 |
| 29 | 136 | 150 | 212 | 300 | 367 | 1051 | 699 | 902 | 1276 | 1805 | 2210 |
| 31 | 136 | 155 | 219 | 310 | 380 | 1126 | 723 | 934 | 1321 | 1868 | 2288 |

Figure 4:
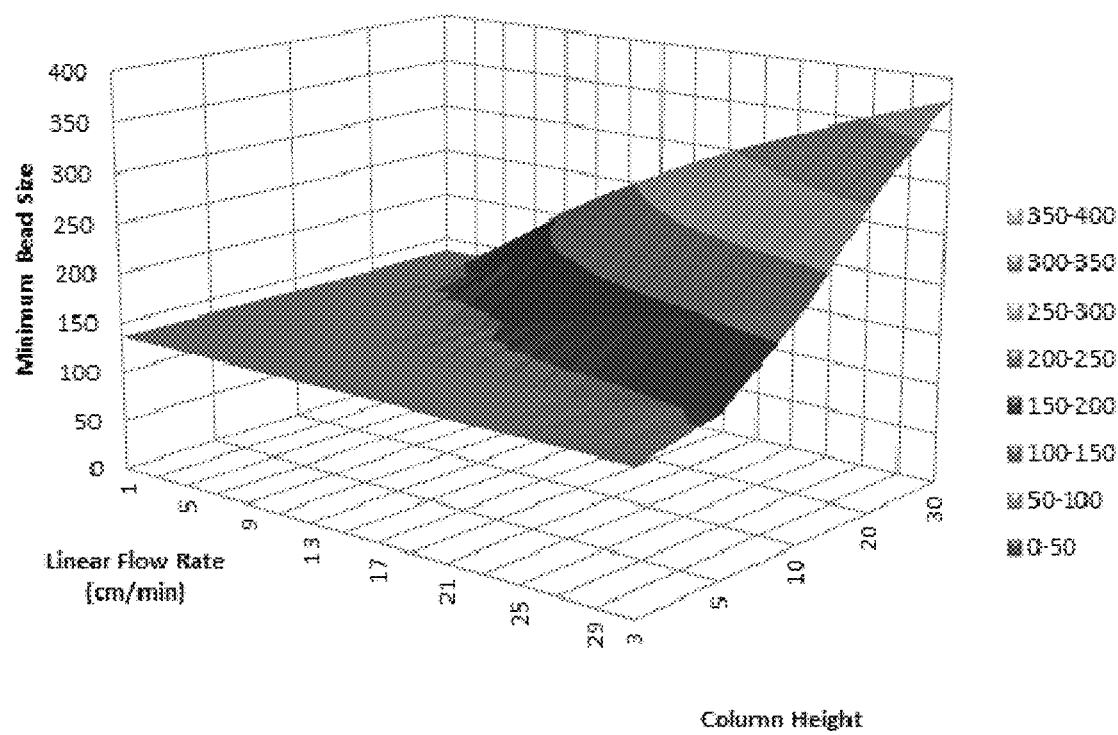
FIG. 4 illustrates the minimum bead size as a function of linear flow and adsorption cartridge column height for a rigid media subject to forced convection.

FIG. 4 represents a plot of Table 5. The plot shows the minimum bead size on the y axis, the linear flow rate on the x axis and the column height on the z axis. FIG. 4 has 6 distinct shades of grey as the bead size cut-off is 136 microns. Therefore, shades representing beads below that size are not represented. (e.g. 0-50 and 50-100).

The data was used to determine the minimum pore opening size of non-bead material such as woven yarns or fibers. The following table (Table 6) provides the corresponding minimum size of pore opening in relation to column height and linear flow rate.

If an adsorption media is compressible, the macroscopic pore size will decrease as a function of flow rate due to the shear stress of flowing blood. A compressible media can be "pre-compressed" to achieve the minimum pore size as calculated in Table 6 for a desired flow rate. For a loosely packed compressible media, the macroscopic pore size must not decrease below the values in the Table 6 under flow conditions, otherwise the pressure of the system will increase that could lead to hemolysis and macrophages would also be filtered out.

In addition to the determining particle size and/or macroscopic pore size, the diameter (e.g., inner diameter) of the extracorporeal filter cartridge can determined. Table 7 provides useful cartridge diameters necessary to achieve the needed linear flow rate at a specific volumetric flow rate.

TABLE 6

Macroscopic Pore Sizes for Non-Bead Material

| | Macroscopic Pore Size | | | | | | Macroscopic Pore Size | | | | |
|---|---|---|---|---|---|---|---|---|---|---|---|
| | L (column height in cm) | | | | | | L (column height in cm) | | | | |
| u (cm/min) | 3 | 5 | 10 | 20 | 30 | u (cm min) | 3 | 5 | 10 | 20 | 30 |
| 1 | 21 | 21 | 21 | 21 | 21 | 1 | 21 | 21 | 21 | 21 | 21 |
| 3 | 21 | 21 | 21 | 21 | 21 | 76 | 29 | 38 | 53 | 75 | 92 |
| 5 | 21 | 21 | 21 | 21 | 24 | 151 | 41 | 53 | 75 | 106 | 130 |
| 7 | 21 | 21 | 21 | 23 | 28 | 226 | 50 | 65 | 92 | 129 | 159 |
| 9 | 21 | 21 | 21 | 26 | 32 | 301 | 58 | 75 | 106 | 149 | 183 |
| 11 | 21 | 21 | 21 | 29 | 35 | 376 | 65 | 83 | 118 | 167 | 205 |
| 13 | 21 | 21 | 22 | 31 | 38 | 451 | 71 | 91 | 129 | 183 | 224 |
| 15 | 21 | 21 | 24 | 33 | 41 | 526 | 76 | 99 | 140 | 197 | 242 |
| 17 | 21 | 21 | 25 | 36 | 43 | 601 | 82 | 106 | 149 | 211 | 259 |
| 19 | 21 | 21 | 27 | 38 | 46 | 676 | 87 | 112 | 158 | 224 | 274 |
| 21 | 21 | 21 | 28 | 39 | 48 | 751 | 91 | 118 | 167 | 236 | 289 |
| 23 | 21 | 21 | 29 | 41 | 51 | 826 | 96 | 124 | 175 | 247 | 303 |
| 25 | 21 | 22 | 30 | 43 | 53 | 901 | 100 | 129 | 183 | 258 | 317 |
| 27 | 21 | 22 | 32 | 45 | 55 | 976 | 104 | 135 | 190 | 269 | 329 |
| 29 | 21 | 23 | 33 | 46 | 57 | 1051 | 108 | 140 | 197 | 279 | 342 |
| 31 | 21 | 24 | 34 | 48 | 59 | 1126 | 112 | 144 | 204 | 289 | 354 |

TABLE 7

Cartridge Diameters

| | Diameter of Cartridge (cm) | | | | | | Diameter of Cartridge (cm) | | | | | |
|---|---|---|---|---|---|---|---|---|---|---|---|---|
| | Desired Volumetric Flow Rate (ml/min) | | | | | | Desired Volumetric Flow Rate (ml/min) | | | | | |
| u (cm/min) | 50 | 100 | 150 | 300 | 500 | 1000 | u (cm/min) | 500 | 1000 | 2000 | 3000 | 4000 | 5000 |
| 1 | 14.1 | 20.0 | 24.5 | 34.6 | 44.7 | 63.2 | 1 | 44.7 | 63.2 | 89.4 | 109.5 | 126.5 | 141.4 |
| 3 | 8.2 | 11.5 | 14.1 | 20.0 | 25.8 | 36.5 | 76 | 5.1 | 7.3 | 10.3 | 12.6 | 14.5 | 16.2 |
| 5 | 6.3 | 8.9 | 11.0 | 15.5 | 20.0 | 28.3 | 151 | 3.6 | 5.1 | 7.3 | 8.9 | 10.3 | 11.5 |
| 7 | 5.3 | 7.6 | 9.3 | 13.1 | 16.9 | 23.9 | 226 | 3.0 | 4.2 | 5.9 | 7.3 | 8.4 | 9.4 |
| 9 | 4.7 | 6.7 | 8.2 | 11.5 | 14.9 | 21.1 | 301 | 2.6 | 3.6 | 5.2 | 6.3 | 7.3 | 8.2 |
| 11 | 4.3 | 6.0 | 7.4 | 10.4 | 13.5 | 19.1 | 376 | 2.3 | 3.3 | 4.6 | 5.6 | 6.5 | 7.3 |

TABLE 7-continued

Cartridge Diameters

| | Diameter of Cartridge (cm) | | | | | | Diameter of Cartridge (cm) | | | | | |
|---|---|---|---|---|---|---|---|---|---|---|---|---|
| | Desired Volumetric Flow Rate (ml/min) | | | | | | Desired Volumetric Flow Rate (ml/min) | | | | | |
| u (cm/min) | 50 | 100 | 150 | 300 | 500 | 1000 | u (cm/min) | 500 | 1000 | 2000 | 3000 | 4000 | 5000 |
| 13 | 3.9 | 5.5 | 6.8 | 9.6 | 12.4 | 17.5 | 451 | 2.1 | 3.0 | 4.2 | 5.2 | 6.0 | 6.7 |
| 15 | 3.7 | 5.2 | 6.3 | 8.9 | 11.5 | 16.3 | 526 | 1.9 | 2.8 | 3.9 | 4.8 | 5.5 | 6.2 |
| 17 | 3.4 | 4.9 | 5.9 | 8.4 | 10.8 | 15.3 | 601 | 1.8 | 2.6 | 3.6 | 4.5 | 5.2 | 5.8 |
| 19 | 3.2 | 4.6 | 5.6 | 7.9 | 10.3 | 14.5 | 676 | 1.7 | 2.4 | 3.4 | 4.2 | 4.9 | 5.4 |
| 21 | 3.1 | 4.4 | 5.3 | 7.6 | 9.8 | 13.8 | 751 | 1.6 | 2.3 | 3.3 | 4.0 | 4.6 | 5.2 |
| 23 | 2.9 | 4.2 | 5.1 | 7.2 | 9.3 | 13.2 | 826 | 1.6 | 2.2 | 3.1 | 3.8 | 4.4 | 4.9 |
| 25 | 2.8 | 4.0 | 4.9 | 6.9 | 8.9 | 12.6 | 901 | 1.5 | 2.1 | 3.0 | 3.6 | 4.2 | 4.7 |
| 27 | 2.7 | 3.8 | 4.7 | 6.7 | 8.6 | 12.2 | 976 | 1.4 | 2.0 | 2.9 | 3.5 | 4.0 | 4.5 |
| 29 | 2.6 | 3.7 | 4.5 | 6.4 | 8.3 | 11.7 | 1051 | 1.4 | 2.0 | 2.8 | 3.4 | 3.9 | 4.4 |
| 31 | 2.5 | 3.6 | 4.4 | 6.2 | 8.0 | 11.4 | 1126 | 1.3 | 1.9 | 2.7 | 3.3 | 3.8 | 4.2 |

Another factor to consider is the total blood volume used with an extracorporeal device. For instance, the total volume removed from the body during an extracorporeal circulation treatment is typically no more than 8-10% of the patient's blood. For an average adult, this equates to 500 ml of blood. A typical dialysis cartridge and tubing blood volume can range from 250-300 ml. If a dialysis cartridge is used in series with an adsorption cartridge, then the blood volume of the adsorption cartridge should be no more than 200 ml. The practical dimensions for an adsorption cartridge of the present invention is provided in Table 8.

TABLE 8

Blood Volume of Packed Cartridge (ml)-0.36 void volume ratio

| | Column Height (cm) | | | | |
|---|---|---|---|---|---|
| Diameter | 3 | 5 | 10 | 20 | 30 |
| 1 | 0.84834 | 1.4139 | 2.8278 | 5.6556 | 8.4834 |
| 5 | 21.2085 | 35.3475 | 70.695 | 141.39 | 212.085 |
| 10 | 84.834 | 141.39 | 282.78 | 565.56 | 848.34 |
| 15 | 190.8765 | 318.1275 | 636.255 | 1272.51 | 1908.765 |
| 20 | 339.336 | 565.56 | 1131.12 | 2262.24 | 3393.36 |

This example provides exemplary embodiments of the adsorption media and adsorption cartridge describe above. The adsorption media can be used in extracorporeal therapies with volumetric flow rate of up to 5000 ml/min and linear flow rates of up to 1000 cm/min.

Example 4. Blood Filters for Removal of Hepatitis C Virus and Hepatitis B Virus

This example provides an extracorporeal filter cartridge that is used to remove Hepatitis C virus and Hepatitis B virus. In this example, the adsorption media is mixed. The mixed media comprises a 70:30 ratio of heparinzed polyethylene beads:protein A fixed to a cellulose gel.

The heparinzed PE beads have covalent end-point attachment of nitrous acid degraded heparin onto aminated PE beads. The heparinized PE beads contain 2.6 mg heparin/g beads.

Covalent end-point attachment of nitrous acid degraded heparin onto aminated PE beads is prepared using 0.1 M acetate buffer pH 4.0 (100 ml) and nitrous acid degraded heparin (1.6 g). After shaking for 15 min, NaBH$_3$CN (100 mg) dissolved in 0.1 M acetate buffer pH 4.0 (10 ml) is added. The reaction mixture is shaken for 24 h at room temperature and additional NaBH$_3$CN (100 mg) dissolved in 0.1 M acetate buffer pH 4.0 (10 ml) is added, and shaking is continued for another 24 h at room temperature to produce the covalent end-point attachment of heparin.

In 0.5 mL of 0.05 M borate buffer (pH 10.0) is dissolved 4 mg of protein A (Sigma), and 0.01 N NaOH/water is added so as to bring the pH to 10 and make a total volume of 1.0 mL (protein A solution). This protein solution (total amount) is added to 1 mL of an epoxy-activated cellulose gel and the mixture is shaken at 37° C. for 16 hours and washed with a sufficient amount of PBS (10 mM phosphate buffer supplemented with 150 mM sodium chloride) to provide GCL 2000m-Protein A.

The mixed adsorption media is used to remove Hepatitis C virus and Hepatitis B virus from blood.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An ex vivo method for removing bacteria from a whole blood sample taken from a subject who is suspected of being infected with bacteria, wherein the bacteria are known to have a low affinity or no affinity for heparin or heparan sulfate, or its affinity to heparin or heparin sulfate is unknown, the method comprising:

contacting the whole blood sample taken from the subject at a linear flow rate of about 400 cm/min to about 1000 cm/min with an adsorption media to allow the formation of an adhering complex, wherein the adsorption media is a solid substrate of high surface area having at least one polysaccharide adsorbent comprising heparin or heparan sulfate on the surface thereof, wherein the solid substrate comprises a plurality of rigid polymer beads, wherein the rigid polymer bead is a member selected from the group consisting of polyurethane, polymethylmethacrylate, polyethylene or co-polymers of ethylene and other monomers, polyethylene imine, polypropylene, and polyisobutylene, and wherein the minimum neck size is 21 microns, wherein the bacteria is a gram-negative bacteria is a member selected from the group consisting of *Klebsiella pneumoniae*, *Acine-* tobacter baumannii, carbapenem-resistant *Escherichia coli*, and carbapenem-resistant *Klebsiella pneumoniae*; and separating the sample from the adhering complex to produce the sample with a reduced amount of bacteria, wherein the bacteria in the sample is reduced by about 20% to about 99.9%.

2. The method of claim 1, wherein the plurality of rigid polymer beads is a member selected from the group consisting of polyethylene or co-polymers of ethylene and other monomers, polyethylene imine, polypropylene, and polyisobutylene.

3. The method of claim 1, wherein the plurality of rigid polymer beads is polyethylene.

4. The method of claim 1, wherein the plurality of rigid polymer beads is polyethylene imine.

5. The method of claim 1, wherein the at least one polysaccharide absorbent is heparan sulfate.

6. The method of claim 1, wherein the at least one polysaccharide absorbent is heparin.

7. The method of claim 1, wherein the plurality of beads are coated with about 0.27 mg to about 10 mg heparin per gram of bead.

8. The method of claim 7, wherein the plurality of bead are coated with 2±0.5 mg heparin per gram of bead.

9. The method of claim 1, wherein the bacteria in the sample is reduced by about 20% to about 40%.

10. The method of claim 1, wherein the bacteria is selected from the group consisting of *Acinetobacter baumannii*, and carbapenem-resistant *Escherichia coli*.

11. The method of claim 10, wherein the bacteria is carbapenem-resistant *Escherichia coli* or carbapenem-resistant *Klebsiella pneumoniae*.

12. The method of claim 10, wherein the contacting step of the sample taken from the subject with the adsorption media is at a linear flow rate of about 1000 cm/min.

13. The method of claim 1, wherein the rigid polymer beads have a diameter of 300 nm to 1 mm.

14. The method of claim 1, wherein the adsorption media is contained within a column having a height and width to reduce pressure and minimize hemolysis.

* * * * *